(12) United States Patent  
Kanan et al.

(10) Patent No.: US 11,475,566 B2  
(45) Date of Patent: Oct. 18, 2022

(54) SYSTEMS AND METHODS TO PROCESS ELECTRONIC IMAGES FOR CONTINUOUS BIOMARKER PREDICTION

(71) Applicant: PAIGE.AI, Inc., New York, NY (US)

(72) Inventors: Christopher Kanan, Rochester, NY (US); Belma Dogdas, Ridgewood, NJ (US); Patricia Raciti, New York, NY (US); Matthew Lee, London (GB); Alican Bozkurt, New York, NY (US); Leo Grady, Darien, CT (US); Thomas Fuchs, New York, NY (US); Jorge S. Reis-Filho, New York, NY (US)

(73) Assignee: PAIGE.AI, Inc., New York, NY (US)

( * ) Notice: Subject to any disclaimer, the term of this patent is extended or adjusted under 35 U.S.C. 154(b) by 0 days.

(21) Appl. No.: 17/410,031

(22) Filed: Aug. 24, 2021

(65) Prior Publication Data

US 2022/0051403 A1 Feb. 17, 2022

Related U.S. Application Data

(63) Continuation of application No. 17/399,422, filed on Aug. 11, 2021.

(Continued)

(51) Int. Cl.
*G06T 7/00* (2017.01)
*G06T 7/11* (2017.01)
(Continued)

(52) U.S. Cl.
CPC .......... *G06T 7/0012* (2013.01); *G06K 9/6256* (2013.01); *G06N 20/00* (2019.01);
(Continued)

(58) Field of Classification Search
CPC ................ G06T 7/0012; G06T 7/11; G06T 2207/20081; G06T 2207/20084; G06T 2207/30024; G06T 2207/30068; G06T 2207/10081; G06T 2207/10088; G06T 2207/10104; G06T 7/73; G06T 2207/30096; G06T 2207/20016; G16H 50/20; G16H 30/40; G06K 9/4671; G06K 9/6256; G06K 2209/05
See application file for complete search history.

(56) References Cited

U.S. PATENT DOCUMENTS

| 2015/0169982 A1* | 6/2015 | Perry | G06K 9/6256 |
| | | | 382/195 |
| 2016/0232425 A1* | 8/2016 | Huang | G06V 10/806 |

(Continued)

*Primary Examiner* — Vu Le
*Assistant Examiner* — Winta Gebreslassie
(74) *Attorney, Agent, or Firm* — Bookoff McAndrews, PLLC.

(57) ABSTRACT

Systems and methods are disclosed for processing digital images to predict at least one continuous value comprising receiving one or more digital medical images, determining whether the one or more digital medical images includes at least one salient region, upon determining that the one or more digital medical images includes the at least one salient region, predicting, by a trained machine learning system, at least one continuous value corresponding to the at least one salient region, and outputting the at least one continuous value to an electronic storage device and/or display.

19 Claims, 11 Drawing Sheets

Related U.S. Application Data

(60) Provisional application No. 63/065,247, filed on Aug. 13, 2020.

(51) Int. Cl.
```
G16H 50/20    (2018.01)
G16H 30/40    (2018.01)
G06V 10/46    (2022.01)
G06K 9/62     (2022.01)
G16H 10/60    (2018.01)
G06N 20/00    (2019.01)
```

(52) U.S. Cl.
CPC .............. *G06T 7/11* (2017.01); *G06V 10/462* (2022.01); *G16H 10/60* (2018.01); *G16H 30/40* (2018.01); *G16H 50/20* (2018.01); *G06T 2207/10081* (2013.01); *G06T 2207/10088* (2013.01); *G06T 2207/10104* (2013.01); *G06T 2207/20081* (2013.01); *G06T 2207/20084* (2013.01); *G06T 2207/30024* (2013.01); *G06T 2207/30068* (2013.01); *G06V 2201/03* (2022.01)

(56) References Cited

U.S. PATENT DOCUMENTS

| | | |
|---|---|---|
| 2016/0260208 A1 | 9/2016 | Rapaka et al. |
| 2017/0270666 A1* | 9/2017 | Barnes ................ G06T 7/12 |
| 2018/0075597 A1 | 3/2018 | Zhou et al. |
| 2018/0315193 A1 | 11/2018 | Paschalakis et al. |
| 2018/0336319 A1 | 11/2018 | Itu et al. |
| 2019/0042828 A1 | 2/2019 | Solanki et al. |
| 2020/0258223 A1* | 8/2020 | Yip ...................... G06T 7/11 |
| 2021/0166785 A1* | 6/2021 | Yip ...................... G16B 30/00 |

\* cited by examiner

SYSTEMS AND METHODS TO PROCESS ELECTRONIC IMAGES FOR CONTINUOUS BIOMARKER PREDICTION

RELATED APPLICATION(S)

This application is a continuation of and claims the benefit of priority to U.S. Nonprovisional patent application Ser. No. 17/399,422, filed on Aug. 11, 2021, which claims priority to U.S. Provisional Application No. 63/065,247 filed Aug. 13, 2020, each of which are incorporated herein by reference in their entireties.

FIELD OF THE DISCLOSURE

Various embodiments of the present disclosure pertain generally to image processing methods. More specifically, particular embodiments of the present disclosure relate to systems and methods for continuous biomarker prediction based on processing images of tissue specimens.

BACKGROUND

Biomarkers are measurable indicators of disease state that may help guide treatment. Biomarker interpretation may be binary (present/absent) or continuous, the latter providing greater information to the clinician and patient. In oncology, many biomarkers are genomic in nature and furthermore, are measured from formalin fixed paraffin embedded (FFPE) tissue found within histology blocks in tumor tissue visualized using hematoxylin and eosin (H&E) or other tissue staining schemes. Some examples may include OncoType DX, Breast Cancer Index, and the Prosigna Breast Cancer Prognostic Gene Signature Assay, all of which provide continuous measures for recurrence of breast cancer, as well as homologous recombination deficiency (HRD), which indicates the severity of the mutations present that impair normal DNA damage repair, and tumor mutation burden (TMB), which measures the total number of mutations found in the DNA of cancer cells.

These biomarkers and many others are measured from FFPE tumor tissue. This may require comprehensive histologic assessment of salient regions (e.g., invasive tumor, stroma around an invasive tumor, the invasive tumor margin, etc.) by a pathologist. After histologic assessment, which may take days, for genomic tests the tissue may be sent (e.g., mailed) to an external lab to perform tumor extraction and molecular testing. These steps are expensive, have aspects of subjectivity in terms of pathologic assessment of the tissue specimen, and may result in a large time lag between tissue removal and the results of the assay being sent to the clinician and patient.

One or more exemplary embodiments of the present disclosure may overcome the problems described above.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing digital images to predict at least one continuous value.

A computer-implemented method for method for processing digital images to predict at least one continuous value comprising receiving one or more digital medical images, determining whether the one or more digital medical images includes at least one salient region, upon determining that the one or more digital medical images includes the at least one salient region, predicting, by a trained machine learning system, at least one continuous value corresponding to the at least one salient region, and outputting the at least one continuous value to an electronic storage device and/or display.

A computer system for processing digital images to predict at least one continuous value for one or more digital medical images comprising at least one memory storing instructions, and at least one processor configured to execute the instructions to perform operations comprising access the at least one memory and execute processor-readable instructions, which when executed by the at least one processor configures the at least one processor to perform a plurality of functions, including functions for: receiving one or more digital medical images, determining whether the one or more digital medical images includes at least one salient region, upon determining that the one or more digital medical images includes the at least one salient region, predicting, by a trained machine learning system, at least one continuous value corresponding to the at least one salient region, and outputting the at least one continuous value to an electronic storage device and/or display.

A non-transitory computer-readable medium storing instructions that, when executed by a processor, cause the processor to perform operations for processing digital images to predict at least one continuous value for one or more digital medical images comprising: receiving one or more digital medical images, determining whether the one or more digital medical images includes at least one salient region, upon determining that the one or more digital medical images includes the at least one salient region, predicting, by a trained machine learning system, at least one continuous value corresponding to the at least one salient region, and outputting the at least one continuous value to an electronic storage device and/or display.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
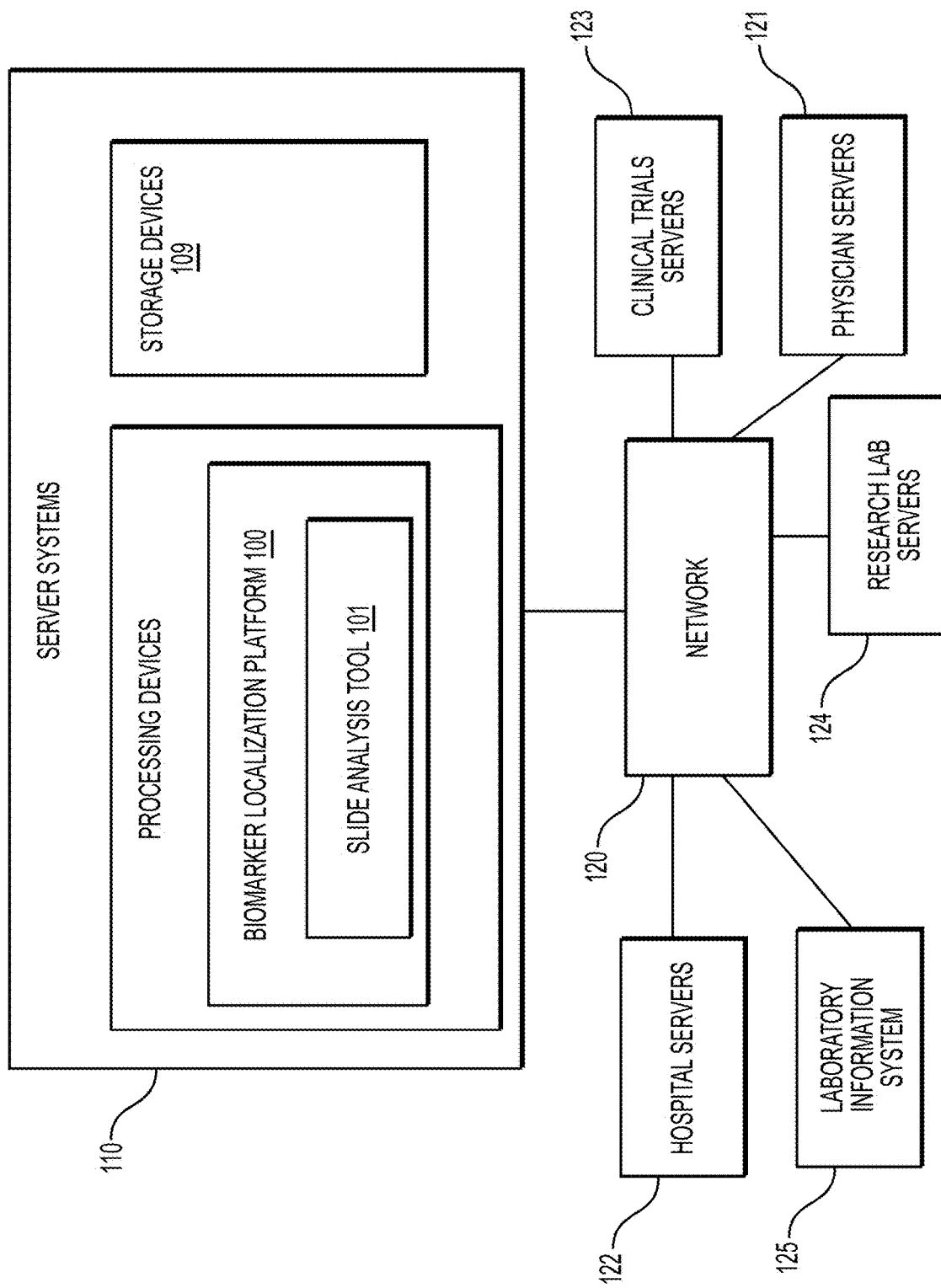
FIG. 1A illustrates an exemplary block diagram of a system and network for predicting a value for a tumor in a tissue specimen, according to techniques presented herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

The present disclosure relates to using machine learning to predict one or more continuous biomarkers from a patient's medical image data. Although the continuous biomarkers or values used for training a system may come from pathologic assessment or genomic testing, exemplary embodiments may be used after training to predict the continuous values without these costly steps. Techniques presented herein may examine the spatial profile of the specimen to incorporate relevant information which is either done explicitly (e.g., detecting tumors at the positive margin or LVSI directly), implicitly (e.g., using spatial mechanisms integrated into the system), or using a combination of both. These computational biomarkers may be used immediately after processing the tissue at a hospital and may enable genomic testing to be avoided. Continuous biomarkers enable a clinician and patient to make better judgments regarding the efficacy of a treatment. This technology has the potential to improve treatment and democratize care.

For predicting many biomarkers, the overall mutational profile of a resected tumor might not suffice for prediction or prognosis because heterogeneity may exist with respect to the mutations harbored by individual cancer cells. The most dominant clone within a resected tumor might not represent the clone most likely to metastasize or persist in the patient after resection. Coupling meaningful spatial locations of tumor cells within a given resection specimen with a mutational profile has the potential to be more informative in guiding treatment than simply targeting the most common mutation found within the tumor. For example, the mutational profile of cancer cells specifically found within lymphovascular spaces or within lymph nodes might harbor more valuable genetic treatment targets than the mutational profile of cancer found within the matrix of tissue; tumor cells in lymphovascular spaces or lymph nodes might tend to have mutations that allow for lymphovascular space invasion (LVSI) and lymph node involvement, and thus, may represent the greatest risk to the patient in terms of future spread and recurrence. In addition, tumor cells unintentionally transected at a tissue margin during a resection ("positive margin") again may pose the greatest threat to patient in terms of recurrence and spread; thus, the mutational profile of these cells specifically might be more useful to the treating oncologist than the mutational profile of the excised tumor mass. However, physical isolation of these cells is a manual, labor intensive process involving detection of the areas of interest, manual removal of the cells, and subjecting the cells of interest to DNA sequencing, which is not feasible.

Exemplary embodiments may include using machine learning to predict continuous scores/values/biomarkers from medical images. Continuous scores may be degree of drug response, level of a specific biomarker, probability of cancer metastasis, years of survival, a diagnostically relevant measurement, etc.

One or more exemplary embodiments may include predicting continuous values from medical images using the spatial characteristics of a medical image.

One or more exemplary embodiments may be implemented in Python with the PyTorch deep learning toolbox. One or more embodiments may be used to predict MammaPrint Index, by using a breast cancer detection system to identify relevant regions of an H&E stained WSI.

One or more exemplary embodiments may be used to predict continuous HER2 scores and counting of mitoses.

FIG. 1A illustrates an exemplary block diagram of a system and network for predicting a value for a tumor in a tissue specimen, according to an exemplary embodiment of the present disclosure.

Specifically, FIG. 1A illustrates an electronic network 120 that may be connected to servers at hospitals, laboratories, veterinarians, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handhold mobile devices. According to an exemplary embodiment of the present disclosure, the electronic network 120 may also be connected to server systems 110, which may include processing devices that are configured to implement a biomarker localization platform 100, which includes a slide analysis tool 101 for determining specimen property or image property information pertaining to digital pathology image(s), and using machine learning to determine whether a disease or infectious agent is present, according to an exemplary embodiment of the present disclosure.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for biomarker localization platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information systems 125.

Figure 1B:
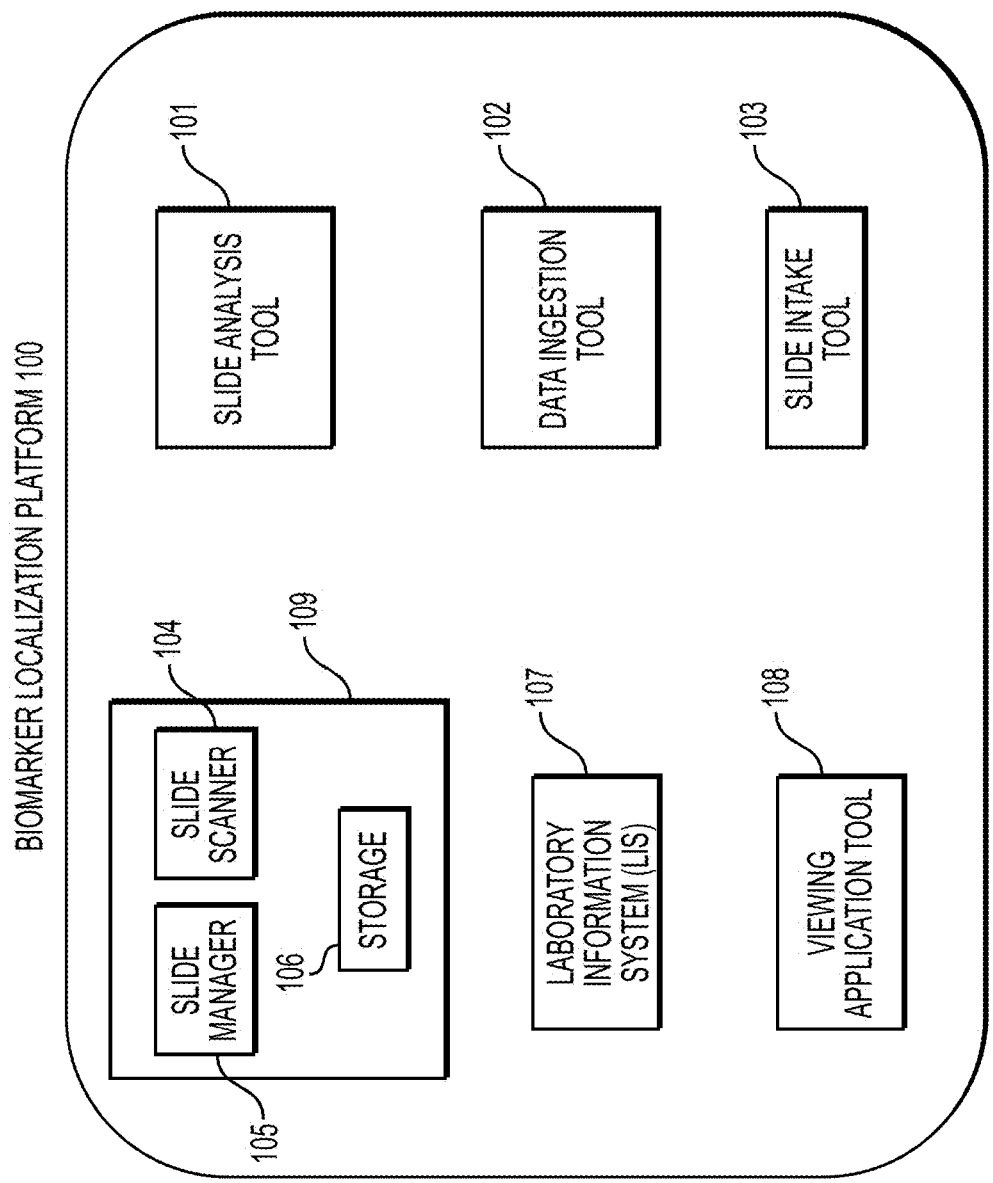
FIG. 1B illustrates an exemplary block diagram of a biomarker localization platform, according to techniques presented herein.

FIG. 1B illustrates an exemplary block diagram of a biomarker localization platform 100 for determining specimen property or image property information pertaining to digital pathology image(s), using machine learning. The biomarker localization platform 100 may include a slide analysis tool 101, a data ingestion tool 102, a slide intake tool 103, a slide scanner 104, a slide manager 105, a storage 106, a laboratory information system 107 and a viewing application tool 108.

The slide analysis tool 101, as described below, refers to a process and system for determining data variable property or health variable property information pertaining to digital pathology image(s). Machine learning may be used to classify an image, according to an exemplary embodiment. The slide analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices 109. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
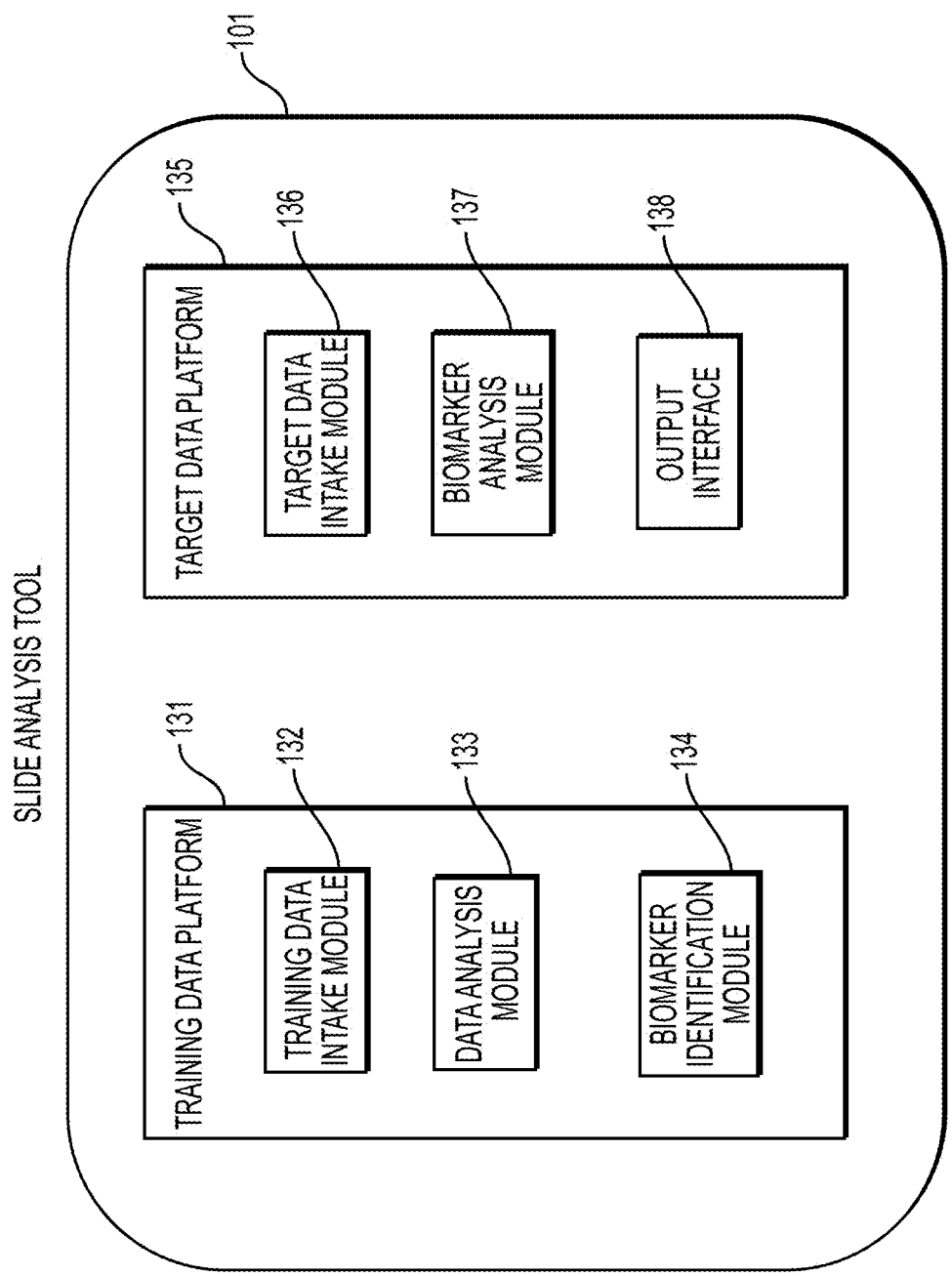
FIG. 1C illustrates an exemplary block diagram of a slide analysis tool, according to techniques presented herein.

FIG. 1C illustrates an exemplary block diagram of a slide analysis tool 101, according to an exemplary embodiment of the present disclosure. The slide analysis tool 101 may include a training data platform 131 and/or a target data platform 135.

According to one embodiment, the training data platform 131 may include a training data intake module 132, a data analysis module 133, and a relationship identification module 134.

The training data platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124 and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training data intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. The dataset may be kept on a digital storage device. The data analysis module 133 may identify quality control (QC) issues (e.g., imperfections) for the training datasets at a global or local level that may greatly affect the usability of a dataset. For example, the quality score determiner module may use information about an entire dataset, e.g., the dataset type, the overall quality of the cut of the specimen, the overall quality of the dataset itself, or pathology slide characteristics, and determine an overall quality score for the dataset. The relationship identification module 134 may analyze health variables and/or data variables and determine whether a determined relationship has an irregular trend. It is useful to identify whether a relationship has an irregular trend, as trends may be used for future relationship predictions, and may trigger an alert to a user.

According to one embodiment, the target data platform 135 may include a target data intake module 136, a biomarker analysis module 137, and an output interface 138. The target data platform 135 may receive a target image and apply the machine learning model to the received from any one or any combination of the server systems 110, physician servers 121, hospital servers 122, clinical trial servers 123, research lab servers 124, and/or laboratory information systems 125. The target data intake module 136 may receive a target dataset corresponding to a target health variable or a data variable. The biomarker analysis module 137 may apply the machine learning model to the target dataset to determine a characteristic of the target health variable or a data variable. For example, the biomarker analysis module 137 may detect a trend of the target relationship. The biomarker analysis module 137 may also apply the machine learning model to the target dataset to determine a quality score for the target dataset. Further, the biomarker analysis module 137 may apply the machine learning model to the target dataset to determine whether the target health variable or a data variable is present in a determined biomarker.

The output interface 138 may be used to output information about the target data and the determined biomarker (e.g., to a screen, monitor, storage device, web browser, etc.).

Figure 2:
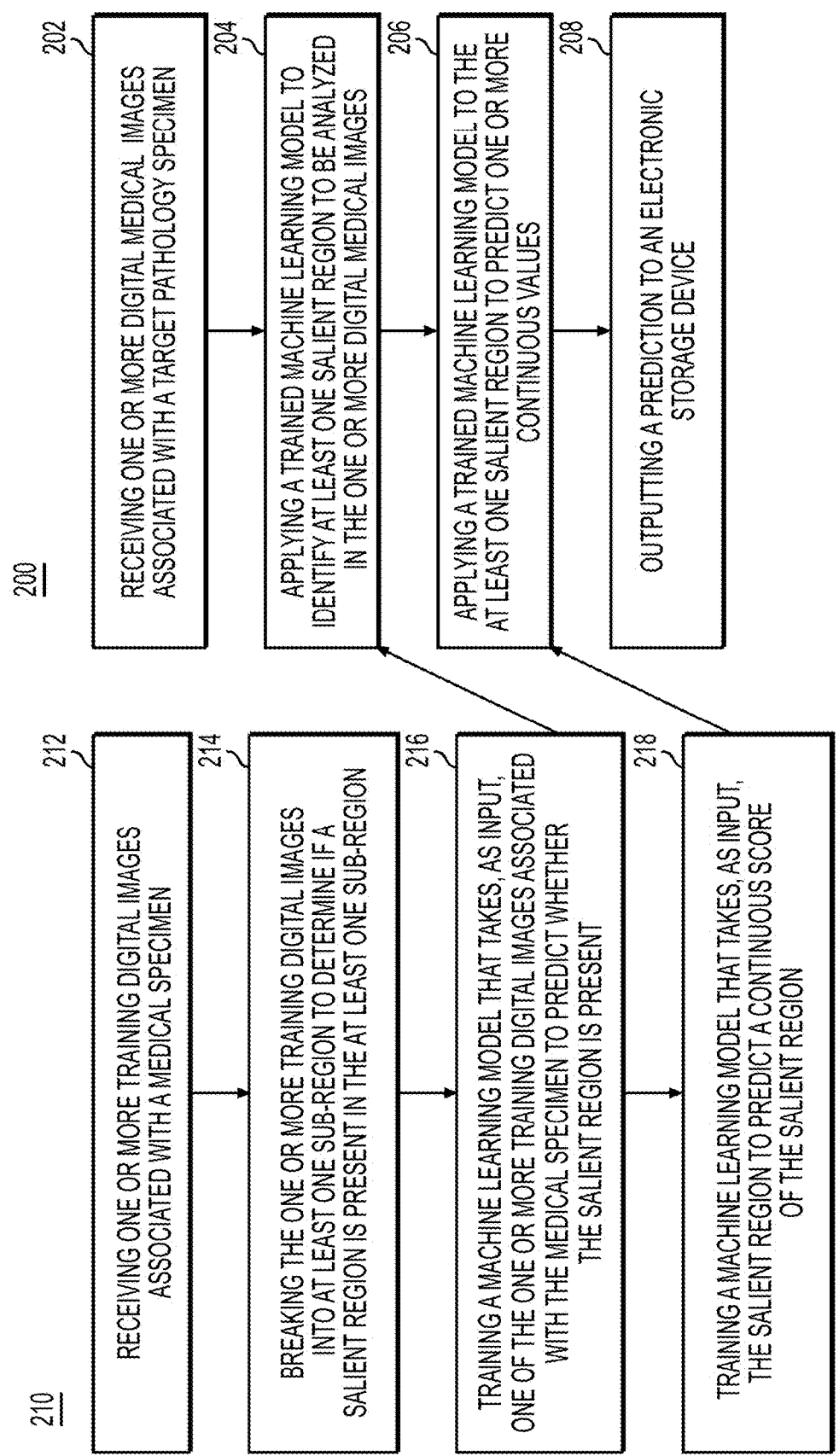
FIG. 2 is a flowchart illustrating an exemplary method for predicting a value for a tumor in a tissue specimen, according to techniques presented herein.

FIG. 2 is a flowchart illustrating an exemplary method for predicting a value for a tumor in a tissue specimen, according to an exemplary embodiment of the present disclosure. For example, an exemplary training method 200 (e.g., steps 202-208) and an exemplary use method 210 (e.g., steps 212-216) may be performed by slide analysis tool 101 automatically or in response to a request from a user.

According to an exemplary embodiment, there may be three components in method 200. In step 202, the method may include receiving one or more digital medical images (e.g., whole slide image (WSI) of a pathology specimen, magnetic resonance imaging (MRI), computed tomography (CT), positron emission tomography (PET), mammogram, etc.) associated with a target pathology specimen into a digital storage device (e.g., hard drive, network drive, cloud storage, RAM, etc.). Optionally, patient information may also be ingested, e.g., age, ethnicity, ancillary test results, etc.

In step 204, the method may include identifying at least one salient region to be analyzed in the one or more digital medical images. A salient region may comprise a tissue or blood region associated with a pathological condition, a cancerous region, one or more biomarkers, specific cell types, particular protein presence and/or levels, at least one drug response indicator, or other searched indicator or relevant diagnostic measurement. The salient region may be associated with predetermined thresholds for any of these values. Identifying the regions may be performed manually by a human or automatically using AI. An entire image or specific image regions may be considered salient.

In step 206, the method may include applying a trained machine learning model to one of the one or more digital medical images to predict one or more continuous values from the one or more digital images. The inference of the one or more continuous values may be accomplished by machine learning and/or computer vision from the one or more digital medical images. The inference may incorporate spatial information from disparate regions in an image.

In step 208, the method may include outputting a prediction to an electronic storage device. Optionally, a user may be alerted to a presence or an absence of one or more of a set of biomarkers.

The salient region detection module of step 204 and the continuous score prediction module of step 206 are elaborated in detail below and in FIGS. 3 and 4.

In step 212, the method may include receiving one or more training digital image associated with a medical specimen and an indication of a presence or an absence of a salient region.

In step 214, the method may include breaking the one or more training digital images into at least one sub-region to determine if a salient region is present.

In step 216, the method may include training a machine learning model that takes, as input, one of the one or more training digital images associated with the medical specimen to predict whether the salient region is present.

In step 218, the method may include training a machine learning model that takes, as input, the salient region to predict a continuous score of the salient region.

For training the machine learning system, one or more of the images may be paired with information about one or more continuous values (e.g., biomarkers from genomic testing, biomarkers from immunohistochemistry (IHC) results analyzed by a pathologist, cell counts of specific cell types, patient survival in months after image acquisition, degree of drug response, protein expression levels, measurements of physical size, etc.). Continuous values may be integers or real numbers.

Salient Region Detection Module

The continuous score of interest may be specific to certain structures within the digital image, and it may be important to identify relevant regions so that they may be included while excluding irrelevant ones. For example, with MRI, PET, or CT data localizing a specific organ of interest may be needed. For histopathology, the continuous score of interest may only be exhibited by an invasive tumor, the stroma around an invasive tumor, the lymphovascular space, an in-situ tumor, etc. This may be important because irrelevant regions may make up the majority of the image. Salient region identification may enable the downstream machine learning system to learn how to detect biomarkers from less annotated data and to make more accurate predictions.

The salient region detection module may output a salient region that was specified by a human annotator using an image segmentation mask, a bounding box, line segment, point annotation, freeform shape, a polygon, or any combination of the aforementioned. Alternatively, this module may be created using machine learning to identify the appropriate locations.

There are two general approaches to using machine learning to create a salient region detector: strongly supervised methods that identify precisely where the biomarker may be found and weakly supervised methods that do not provide a precise location.

For strongly supervised training, the system may need the image and the location of the salient regions that may potentially express the biomarker as input. For 2D images, e.g., whole slide images (WSI) in pathology, these locations may be specified with pixel-level labeling, bounding box-based labeling, polygon-based labeling, or using a corresponding image where the saliency has been identified (e.g., using IHC). For 3D images, e.g., CT and MRI scans, the locations may be specified with voxel-level labeling, using a cuboid, etc., or use a parameterized representation allowing for subvoxel-level labeling, such as parameterized curves or surfaces, or deformed template.

For weakly supervised training, the system may require the image or images and the presence/absence of the salient regions, but the exact location of the salient location might not need to be specified.

Figure 3:
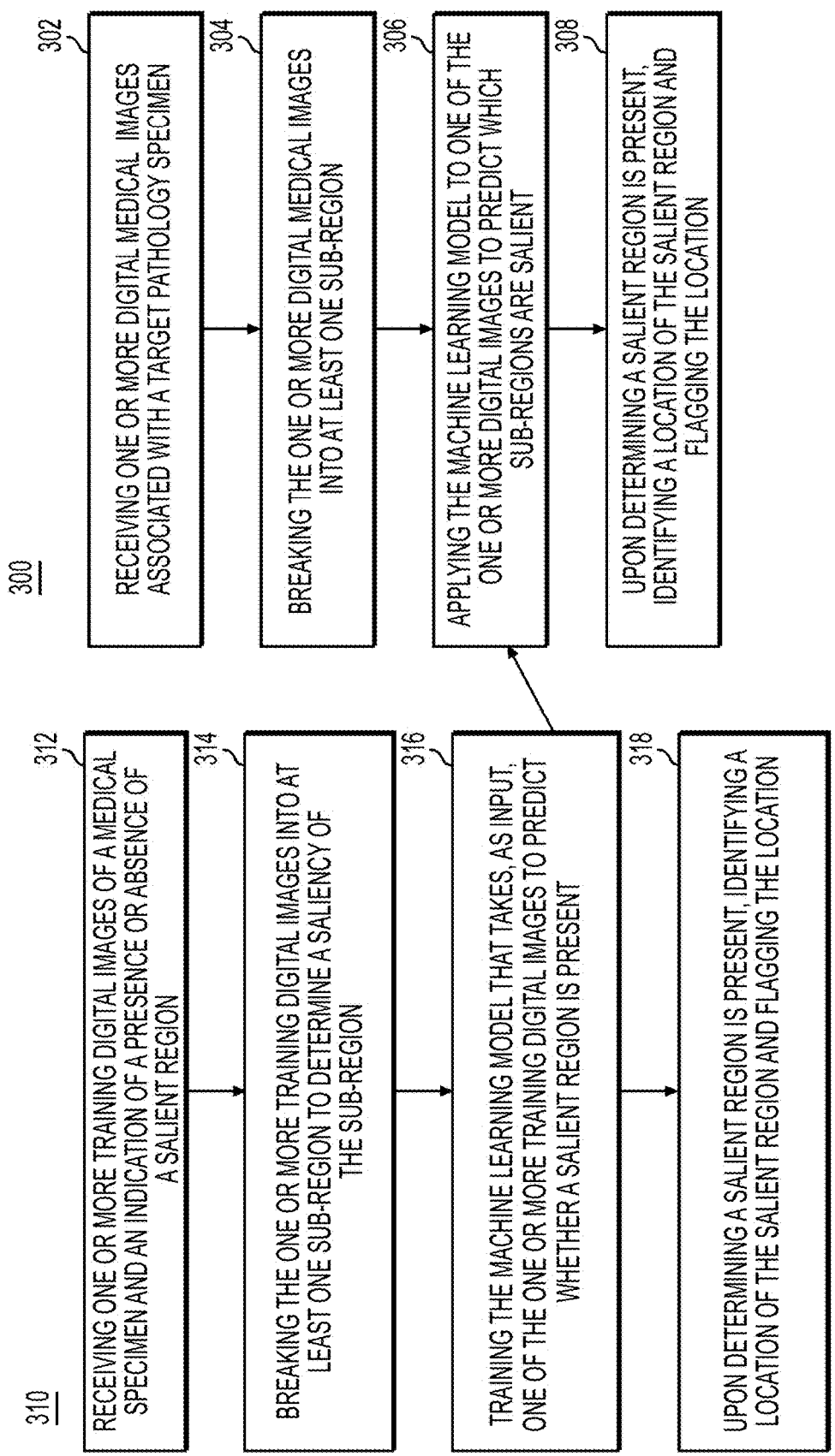
FIG. 3 is a flowchart illustrating an exemplary method for training and using a saliency module, according to techniques presented herein.

FIG. 3 is a flowchart illustrating an exemplary method for training and using a saliency module, according to techniques presented herein. For example, an exemplary training method 300 (e.g., steps 302-306) and an exemplary use method 310 (e.g., steps 312-316) may be performed by slide analysis tool 101 automatically or in response to a request from a user.

In step 302, the method may include receiving one or more training digital images of a medical specimen (e.g., histology, CT, MRI, etc.) into a digital storage device (e.g., hard drive, network drive, cloud storage, RAM, etc.) and an indication of a presence or an absence of a salient region (e.g., invasive cancer present, LVSI, in situ cancer, etc.) within the image.

In step 304, the method may include breaking the one or more training digital images into at least one sub-region to determine a saliency of the sub-region. The sub-regions may then have their saliency determined. Regions may be specified in a variety of methods, including creating tiles of the image, segmentations based on edge/contrast, segmentations via color differences, segmentations based on energy minimization, supervised determination by the machine learning model, EdgeBoxes, etc.

In step 306, the method may include training a machine learning model that takes, as input, one or the one or more training digital images associated with a pathology specimen and predicts whether a salient region is present. Many methods may be used to learn which regions are salient, including but not limited to:
  a. Weak supervision—training a machine learning model (e.g., multi-layer perceptron (MLP), convolutional neural network (CNN), graph neural network, support vector machine (SVM), random forest, etc.) using multiple instance learning (MIL) using weak labeling of the digital image or a collection of images. The label would correspond to the presence or absence of a salient region.
  b. Bounding box or polygon-based supervision—training a machine learning model (e.g., R-CNN, Faster R-CNN, Selective Search, etc.) using bounding boxes or polygons that specify the sub-regions of the digital image that are salient for the detection of the presence or absence of the biomarker.
  c. Pixel-level or voxel-level labeling (e.g., a semantic or instance segmentation)—training a machine learning model (e.g., Mask R-CNN, U-Net, Fully Convolutional Neural Network, etc.) where individual pixels/voxels are identified as being salient for the detection of the continuous score(s) of interest. Labels may include in situ tumor, invasive tumor, tumor stroma, fat, etc. Pixel-level/voxel-level labeling may be from a human annotator or may be from registered images that indicate saliency. For example, with WSIs of histopathology specimens an H&E image may be registered/aligned with an IHC image identifying salient tissue (e.g., cancerous tissue where the biomarker should be found), where the IHC may be used to determine the salient pixels by looking at image color characteristics.

In step 308, the method may include, upon determining a salient region is present, identifying a location of the salient region and flagging the location.

In step 312, the method may include receiving one or more digital medical images associated with a target pathology specimen into a digital storage device (e.g., hard drive, network drive, cloud storage, RAM, etc.).

In step 314, the method may include breaking the one or more digital medical images into at least one sub-region. Each of the sub-regions may then have their saliency determined (e.g., cancerous tissue for which the biomarker(s) should be identified) using the approach from training.

In step 316, the method may include applying the machine learning model to one of the one or more digital images to predict which sub-regions are salient and may potentially exhibit a continuous score(s) of interest (e.g., cancerous tissue). This may include expanding the region to additional tissue, e.g., detecting an invasive tumor region, determining its spatial extent, and then extracting the stroma around the invasive tumor.

In step 318, the method may include, upon determining a salient region is present, identifying a location of a salient region and flagging the location. Detecting the salient regions may be done using a variety of methods, including but not restricted to:
  d. Running the machine learning model on image sub-regions to generate the prediction for one or more sub-regions.
  e. Using machine learning visualization tools to create a detailed heatmap, e.g., by using class activation maps, GradCAM, etc., and then extracting the relevant regions.

Continuous Score Prediction Module

The continuous score prediction module may use the output of the salient region detector to predict the continuous score(s) associated with the target(s) of interest. It predicts a continuous score while incorporating the spatial characteristics of the salient tissue into the prediction. Spatial characteristics may be important for predicting drug response and outcome. Some drugs may be more effective if over-expression of the biomarker of interest is spatially diffuse, e.g., the anti-HER2 therapy trastuzumab deruxtecan appears to be more effective if over-expression of HER2 proteins are spatially diffuse.

There are two primary ways to create the continuous score prediction module that may use spatial characteristics: 1) end-to-end, and 2) a two-stage prediction system. The end-to-end system may be trained directly from the input image whereas the two-stage system first extracts features from the image and then may use machine learning methods that may incorporate the spatial organization of the features.

End-to-End Continuous Score Prediction Module

Figure 4:
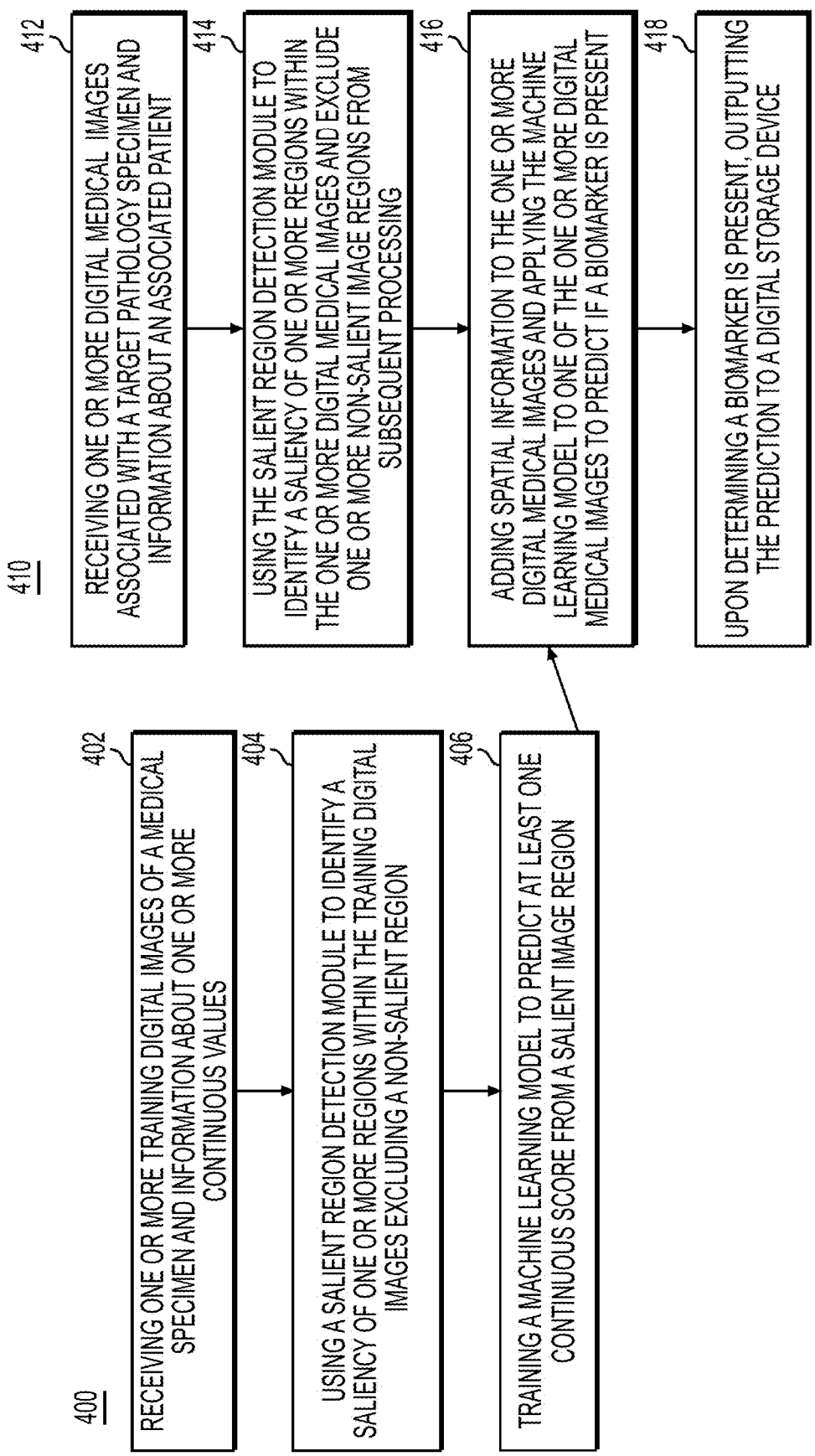
FIG. 4 is a flowchart illustrating an exemplary method for training and using an end-to-end continuous score prediction module, according to techniques presented herein.

FIG. 4 is a flowchart illustrating an exemplary method for training and using an end-to-end continuous score prediction module. For example, an exemplary training method 400 (e.g., steps 402-406) and an exemplary use method 410 (e.g., steps 412-416) may be performed by slide analysis tool 101 automatically or in response to a request from a user.

In step 402, the method may include receiving one or more training digital images of a medical specimen and information about one or more continuous values into a digital storage device (e.g., hard drive, network drive, cloud storage, RAM, etc.). Optionally, patient information may also be ingested, e.g., age, ethnicity, ancillary test results, etc. For training the machine learning system, one or more images may be paired with information about one or more continuous values (e.g., biomarkers from genomic testing, biomarkers from IHC results analyzed by a pathologist, cell counts of specific cell types, patient survival in months after image acquisition, degree of drug response, protein expression levels, etc.).

In step 404, the method may include using a salient region detection module (such as described in FIG. 3) to identify the saliency of one or more regions within the image and exclude non-salient image regions from subsequent processing.

In step 406, the method may include training a machine learning model to predict at least one continuous score from a salient image region. Expression levels may be represented as ordinal values, integers, real numbers, etc. The system would be trained using a regression loss (e.g., mean squared error loss, Huber loss, etc.), an ordinal loss function, or a counting loss function (e.g., Poisson regression loss, negative binomial regression loss, etc.). To incorporate the spatial information, the coordinates of each pixel/voxel may optionally be concatenated to each pixel/voxel. Alternatively, the coordinates may optionally be appended throughout processing (e.g., as done by the CoordConv algorithm). Alternatively, the machine learning algorithm may take spatial information into consideration passively by self-selecting regions in the input to process. If patient information (e.g., age) is also used as an input in addition to medical image data, then that may be fed into the machine learning system as an additional input feature. Machine learning systems that may be trained include, but are not limited to:

f. CNN trained directly with the appropriate continuous score(s) prediction loss function.
 g. CNN with CoordConv layers trained directly with the appropriate continuous score(s) prediction loss function.
 h. Capsule network trained directly with the appropriate continuous score(s) prediction loss function.
 i. MLP trained directly with the appropriate continuous score(s) prediction loss function.
 j. Random Forest trained directly with the appropriate continuous score(s) prediction loss function.
 k. Support Vector Machine trained directly with the appropriate continuous score(s) prediction loss function, etc.

In step 412, the method may include receiving one or more digital medical images (e.g., PET, CT, MRI, histology, etc.) associated with a target pathology specimen and information about an associated patient into a digital storage device (e.g., hard drive, network drive, cloud storage, RAM, etc.). Patient information that may also be ingested may include age, ethnicity, ancillary test results, etc.

In step 414, the method may include using the salient region detection module to identify a saliency of one or more regions within the one or more digital medical images and exclude one or more non-salient image regions from subsequent processing.

In step 416, the method may include adding spatial information to the one or more digital medical images and applying the machine learning model to one of the one or more digital medical images to predict if a biomarker is present.

In step 418, the method may include, upon determining a biomarker is present, outputting the prediction to a digital storage device. Optionally, the method may also include using a visual indicator to alert a user (e.g., a pathologist, histology technician, radiologist etc.) to the level of the continuous scores.

Two-Stage Continuous Score Prediction Module

An alternative to using the single-stage system may be to use a two-stage system. The first stage may use either 1) hand-engineered or pre-trained features or 2) may use machine learning to train a feature extracting module. The second stage predicts continuous scores from features extracted in the first stage.

First stage with hand-engineered or pre-trained feature extraction: If hand-engineered features are used such as SIFT, SURF, ORB, Gabor wavelets, GLCM texture features, etc., then there may be no need to do additional training for feature extraction. Likewise, pre-trained CNN features which may be learned with supervised learning on alternative datasets, learned using an auto-encoder, learned using a generative adversarial network, learned using self-supervised learning also do not require additional training for feature extraction. These features may be extracted from throughout the image in a grid-based or superpixel based manner to produce a plurality of multi-dimensional feature vectors or feature tensors that describe each grid or superpixel location for which they were extracted. Additionally, these features may be collected at multiple resolutions to create pyramids of feature vectors and provide hieratical spatial information. If the salient region detector is used, then grid locations that are not salient may be excluded. For one or more features, the spatial coordinates of that region may optionally be appended to the feature tensor or vector. Alternatively, relative spatial information may be provided, this may include but is not limited to, neighboring regions within the same resolution or parent/child regions from lower/higher resolutions.

First stage with learned feature extractor: For learned feature extraction, it may be necessary to train a machine learning system that may be used to extract a plurality of diagnostic feature vectors or tensors from salient regions within the image.

Figure 5:
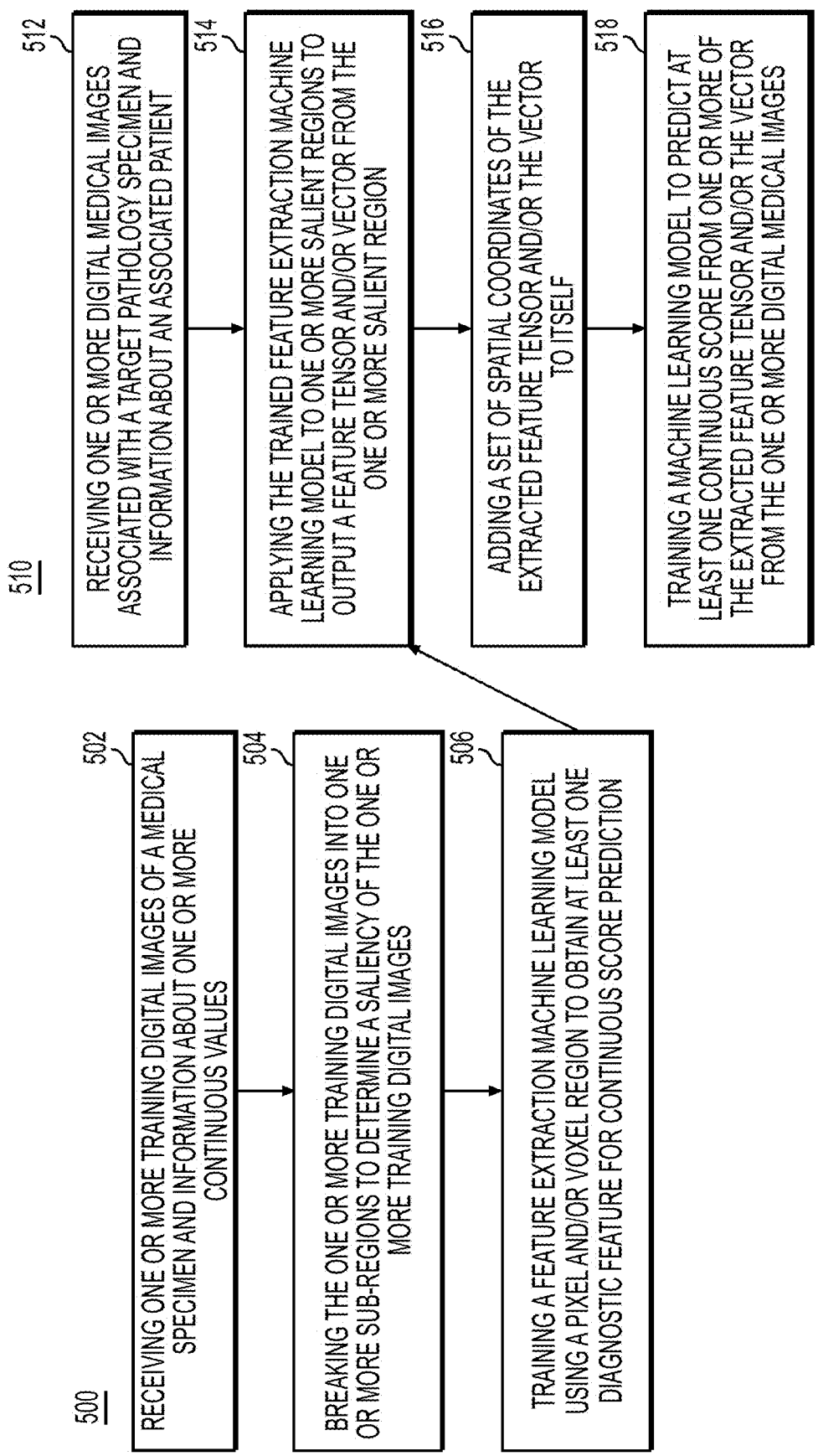
FIG. 5 is a flowchart illustrating an exemplary method for training and using a two-stage continuous score prediction module, according to techniques presented herein.

FIG. 5 is a flowchart illustrating an exemplary method for training a two-stage continuous score prediction module. For example, an exemplary training method 500 for the first stage with a learned feature extractor (e.g., steps 502-508) and an exemplary training method 510 for the second stage (e.g., 512-518) may be performed by slide analysis tool 101 automatically or in response to a request from a user.

In step 502, the method may include receiving one or more training digital images (e.g., PET, CT, MRI, histology, etc.) of a medical specimen and information about one or more continuous values into a digital storage device (e.g., hard drive, network drive, cloud storage, RAM, etc.). For training the machine learning system, one or more images may be paired with information about one or more continuous values (e.g., biomarkers from genomic testing, biomarkers from IHC results analyzed by a pathologist, cell counts of specific cell types, patient survival in months after image acquisition, degree of drug response, protein expression levels, etc.).

In step 504, the method may include breaking the one or more training digital images into one or more sub-regions to determine a saliency of the one or more training digital images. Regions may be specified in a variety of methods, including breaking the image into tiles, segmentations based on edge/contrast, segmentations via color differences, supervised determination by the machine learning model, EdgeBoxes, etc.

Optionally, the method may include using the salient region detection module, as described in FIG. 3 above, to identify the saliency of each region within an image and exclude non-salient image regions from subsequent processing. In some implementations, all non-background regions may be considered salient.

Optionally, the method may also include appending a set of spatial coordinates of each pixel and/or voxel in the image to itself.

In step 506, the method may include training a feature extraction machine learning module using a pixel and/or voxel region to obtain at least one diagnostic feature for continuous score prediction. There are multiple ways to do this, including:

l. Training a 2D or 3D convolutional neural network (CNN) (optionally using CoordConv layers or similar mechanisms to incorporate spatial information) using multi-label or binary machine instance learning (MIL) with one or more cut-offs to create binary labels. For example, given a supervised continuous score y for a patient's digital image data, the multiple binary outputs may each represent a distinct range of continuous values with one binary output for a value y less than a cut-off a, one may be for if y is between a to b, one may be for if y is between b to c, etc. Alternatively, the outputs may be constructed as a series of thresholds, e.g., the binary outputs may be y>a, y>b, y>c, etc.

m. Train a 2D or 3D capsule neural network using multi-label or binary MIL with one or more cut-offs to create binary labels. For example, given a supervised continuous score y for a patient's digital image data, the multiple binary outputs may each represent a distinct range of continuous values with one binary output for a value y less than a cut-off a, one may be for if y is between a to b, one may be for if y is between b to c, etc. Alternatively, the outputs may be constructed as a series of thresholds, e.g., the binary outputs may be y>a, y>b, y>c, etc.

For use of the learned feature extraction module, the trained feature extraction machine learning model may be applied to one or more salient regions of a digital image to output a feature tensor and/or vector for that region.

Second stage for feature tensor/vector aggregation: The second stage may use the feature vectors/tensors extracted in the first stage and then outputs one or more continuous scores of interest, as shown in exemplary training method 510 and described below.

In step 512, the method may include receiving one or more digital medical images (e.g., PET, CT, MRI, histology, etc.) associated with a target pathology specimen and information about an associated patient into a digital storage device (e.g., hard drive, network drive, cloud storage, RAM, etc.). Optionally, patient information may also be ingested, e.g., age, ethnicity, ancillary test results, etc. For training the machine learning system, a plurality of images may be paired with information about one or more continuous values (e.g., biomarkers from genomic testing, biomarkers from IHC results analyzed by a pathologist, cell counts of specific cell types, patient survival in months after image acquisition, degree of drug response, protein expression levels, etc.).

Optionally, the method may include using the salient region detection module of FIG. 3 (and described above) to identify the saliency of each region within the image and exclude non-salient image regions from subsequent processing.

In step 514, the method may include applying the trained feature extraction machine learning model of exemplary training method 500 to one or more salient regions to output a feature tensor and/or a vector from a salient region within the one or more digital medical images. Alternatively, extraction may be done with the hand-engineered or pre-trained first stage feature extraction system.

In step 516, the method may include adding a set of spatial coordinates of the extracted feature tensor and/or the vector to itself, which allows for spatial information to be captured.

In step 518, the method may include training a machine learning model to predict at least one continuous scores from one or more of the extracted feature vector/tensors from one or more images. Expression levels may be represented as ordinal values, integers, real numbers, etc. The system would be trained using a regression loss (e.g., mean squared error loss, Huber loss, etc.), an ordinal loss function, or a counting loss function (e.g., Poisson regression loss, negative binomial regression loss, etc.). If patient information (e.g., age) is also used as an input in addition to medical image data, then that may optionally be fed into the machine learning system as an additional input feature, which may be done by appending it to the feature vectors/tensors (early fusion) or it may be done at a later point in processing by the machine learning system (late fusion). Machine learning systems that may be trained to take as input all feature tensors/vectors for each digital image include, but are not limited to:

n. CNN trained with the appropriate continuous score(s) prediction loss function.

o. CNN with CoordConv layers trained directly with the appropriate continuous score(s) prediction loss function.

p. Recurrent Neural Network (RNN) (e.g., bi-directional RNN, Gated Recurrent Network, Simple RNN, Long short term memory RNN) trained directly with the appropriate continuous score(s) prediction loss function.

q. Graph neural network (e.g., graph convolutional network) trained directly with the appropriate continuous score(s) prediction loss function. Each node of the input graph may have the feature vector/tensor information and the edges of the graph may represent the spatial relationship of each region.

r. Relationship network trained directly with the appropriate continuous score(s) prediction loss function.

s. Capsule network trained directly with the appropriate continuous score(s) prediction loss function.

t. MLP trained directly with the appropriate continuous score(s) prediction loss function.

u. Random Forest trained directly with the appropriate continuous score(s) prediction loss function.

v. Support Vector Machine trained directly with the appropriate continuous score(s) prediction loss function.

w. Etc.

Figure 6A:
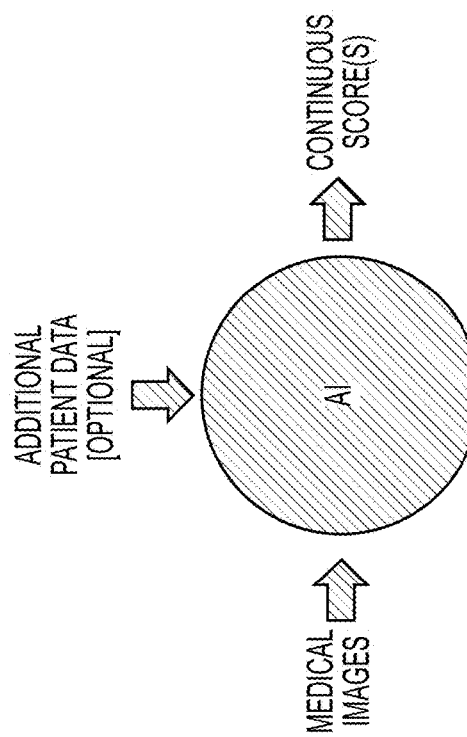
FIGS. 6A and 6B are exemplary workflows with and without using a salient region detection module, according to techniques presented herein.
Figure 6B:
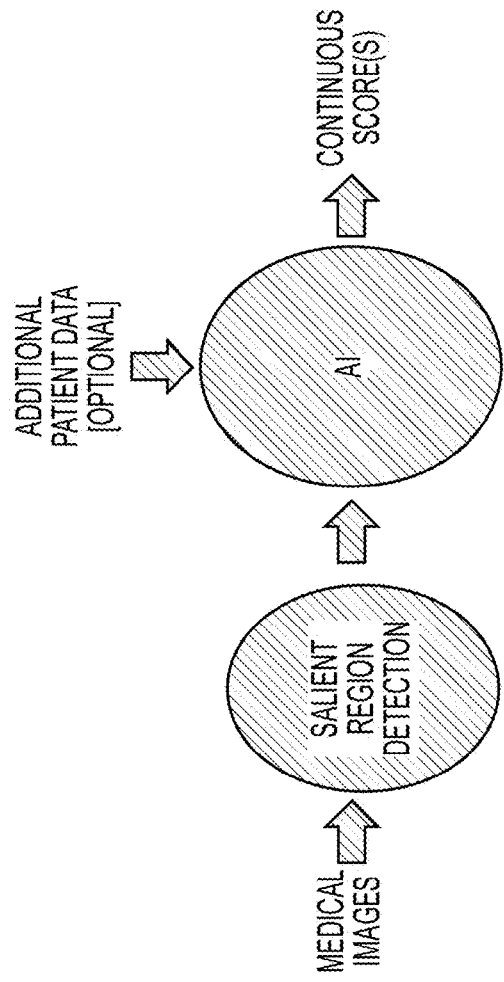

FIGS. 6A and 6B illustrate exemplary workflows of the method of outputting a continuous score, according to one or more embodiments of the present disclosure.

FIG. 6A illustrates an exemplary embodiment of a workflow without using the salient region detection module as described in FIG. 3, above. In the exemplary workflow, medical images are input into an AI module, along with additional patient data (optional). At least one continuous score(s) may be output from the AI module.

FIG. 6B illustrates an exemplary embodiment of a workflow using the salient region detection module as described in FIG. 3, above. In this workflow, medical images are input into a salient region detection module and then into the AI module. Additional patient data may also be put into the AI module. At least one continuous score(s) may be output from the AI module.

Figure 7:
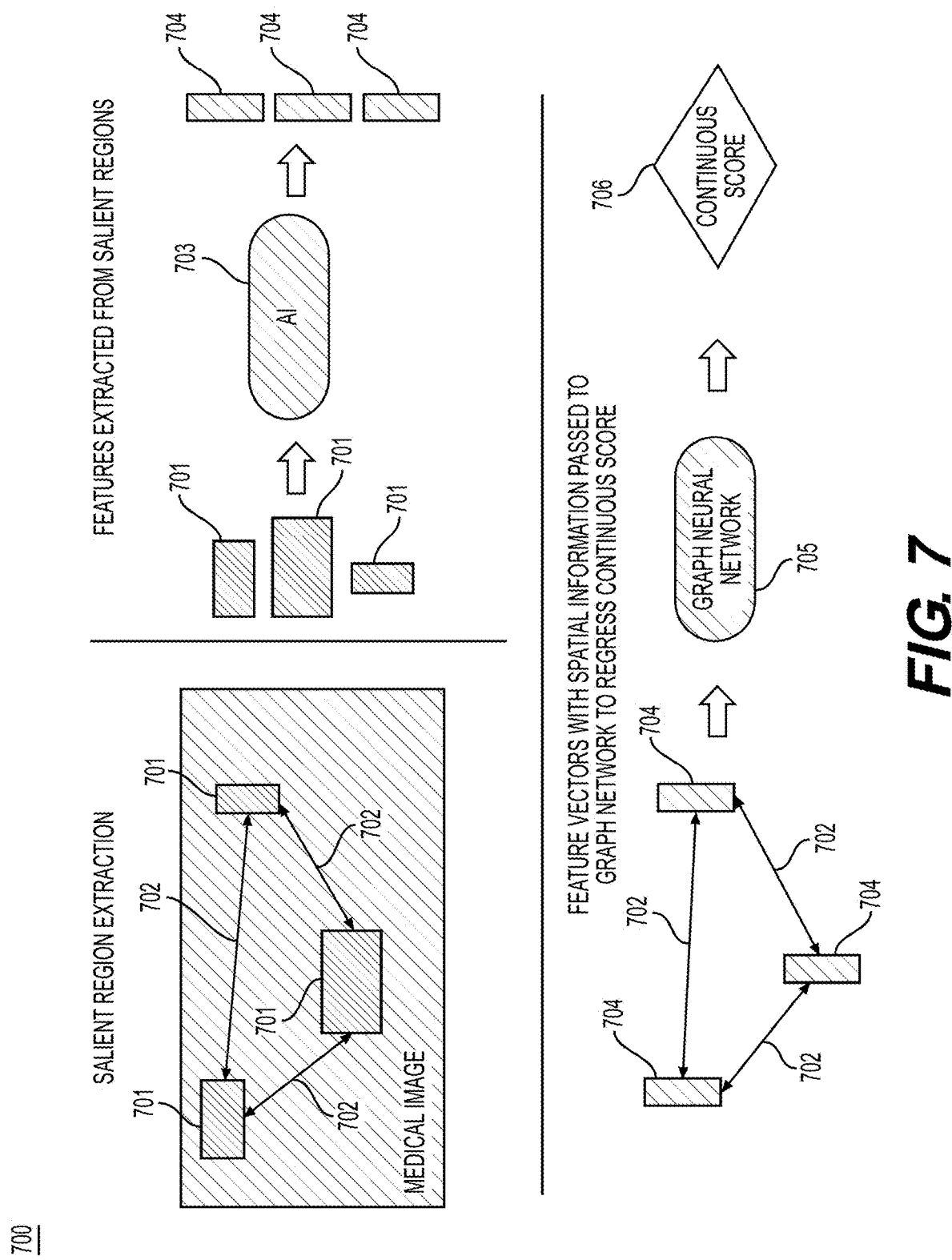
FIG. 7 is an exemplary two-stage workflow using a salient region detection and a graph neural network, according to techniques presented herein.

FIG. 7 illustrates a two-stage exemplary embodiment using a salient region detection module and a graph neural network.

In a salient region extraction, a salient region 701 of a medical image may be separated by spatial information 702. Spatial information 702 may be a relative or an absolute value.

For the features extracted from salient regions, the salient regions 701 may be input to an AI module 703 for an output feature vector 704. A plethora of features may be extracted from one or more of the salient regions.

Feature vectors 704 with spatial information 702 may be passed to a graph neural network 705 for an output of a continuous score 706.

Exemplary Embodiment: Continuous Recurrence Score from WSI for Invasive Breast Cancer After invasive breast cancer is detected, it may be common to perform a genomic assay of the tumor to determine whether to forgo additional treatment, to give the patient endocrine (hormone) therapy, to give the patient adjuvant chemotherapy, and/or some other therapy. These tests assess the risk of recurrence and metastasis of disease after excising the primary tumor using a continuous scoring system. They typically look at genomic information that relates to proliferation, invasion, metastasis, stromal integrity, and angiogenesis.

Figure 8:
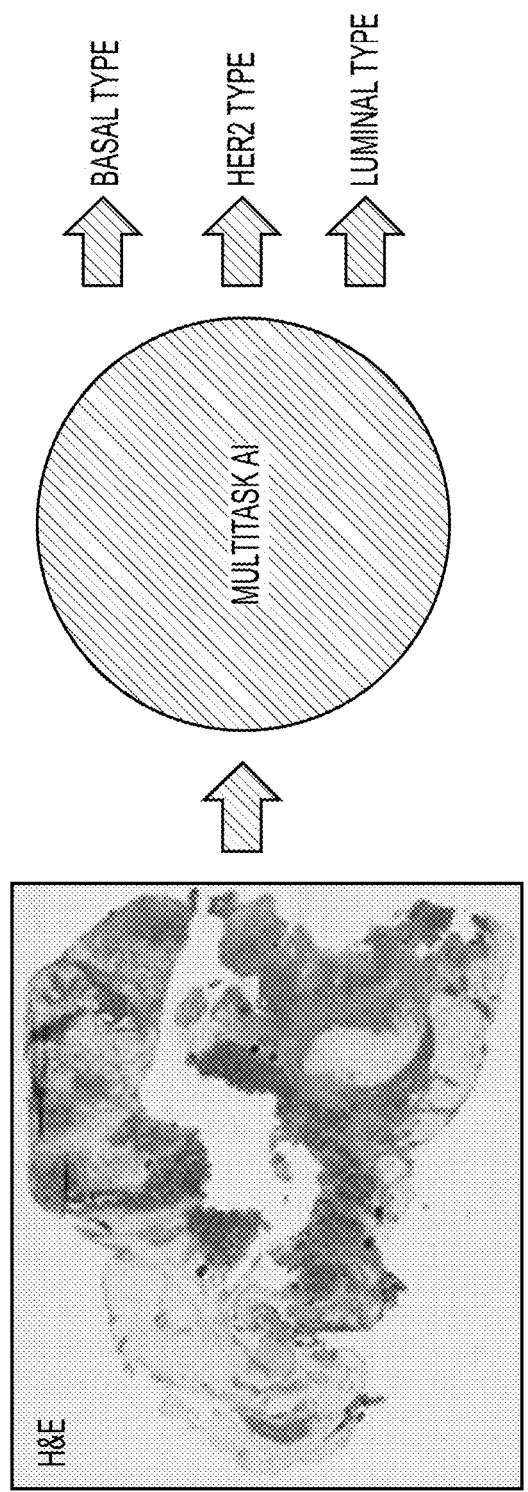
FIG. 8 is an exemplary AI system for predicting a continuous type for invasive breast cancer, according to techniques presented herein.

FIG. 8 is an exemplary workflow, with an image stained with H&E input into a multi-task AI module that may output three continuous values for different scores, such as a basal type continuous value, a HER2 type continuous value, and/or a luminal type continuous value.

The EndoPredict (EPclin) test may be based on RNA expression of 12 genes and combines this genomic information with additional clinical features to predict the 10-year distant recurrence (DR) rate. It assigns a score between 1 and 6, with 6 indicating a high risk and 1 indicting a low risk. Another example test is MammaPrint, which is a 70-gene assay that may use formalin-fixed-paraffin-embedded (FFPE) or fresh tissue, and then may use RNA isolated from the tumor sample to predict a continuous score with values greater than 0 indicating low risk of cancer recurrence and values less than 0 indicating a higher risk of recurrence, which suggests that adjuvant chemotherapy may be needed.

Another example test is the Breast Cancer Index (BCI) test, which analyzes 7 genes to predict cancer recurrence. It produces two scores: The BCI Prognostic score estimates the likelihood of the cancer returning 5 to 10 years after diagnosis on a continuous scale of 0 to 10, with a score of 5.1 to 10 indicating a high risk of recurrence. The BCI Predictive score estimates the likelihood of benefit from taking endocrine therapy for 5 additional years, for 10 years total of endocrine therapy.

Oncotype DX Recurrence Score is another such assay, which looks at the expression of 21 genes within the tumor. It produces a number between 0 to 100 to indicate the risk of cancer recurrence, with a score of greater than 31 indicating a high risk of metastasis and the need for adjuvant chemotherapy with endocrine therapy, a score of 26 to 30 indicating uncertain benefit for adjuvant chemotherapy when used with endocrine therapy, and a score less than 26 indicating that endocrine therapy alone may suffice for treatment after surgery.

The Prosigna Breast Cancer Prognostic Gene Signature Assay (i.e., the PAM50 gene signature) may use RNA from FFPE samples to estimate the risk of distant recurrence for hormone receptor positive breast cancer. It produces a continuous score from 0 to 100, with a higher score indicating a greater risk of recurrence to guide treatment decisions.

All of these tests may share the same limitations: they may require genomic assays, resulting in a delay of up to two weeks after the tissue sample is acquired from a patient. Instead, this embodiment may predict the risk of recurrence directly from WSI, meaning that the clinician may gain the needed information to make treatment decisions in as little as one day after the invasive tumor tissue is removed from a patient. This may be done by training a system that takes as input the WSI of an invasive breast tumor and then predicts any of the continuous scores produced by these genomic assays. Alternatively, it may be used to predict recurrence directly, e.g., this may be done by training it to take as input a WSI of an invasive tumor and predicting months before recurrence if treatment is not given.

1. For training:
   a. Receiving one or more digital WSI of an invasive breast pathology specimen (e.g., histology, etc.) into a digital storage device (e.g., hard drive, network drive, cloud storage, RAM, etc.) and the continuous recurrence score. Optionally, patient information (e.g., age) may be received for each patient.
   b. Optionally, identifying the salience of each region within the WSI, e.g., the invasive tumor, the stroma around the invasive tumor, and/or the lymphovascular space.
   c. Training a machine learning system to predict the continuous recurrence score from the (salient) image regions.
2. For use:
   a. Receiving one or more digital images of an invasive breast cancer pathology specimen (e.g., histology, etc.) into a digital storage device (e.g., hard drive, network drive, cloud storage, RAM, etc.). Optionally, patient information (e.g., age) may be received for each patient.
   b. Optionally, receiving the location of salient region, which may be either automatically or manually specified by an expert.
   c. Applying the trained machine learning system to output a prediction of cancer recurrence.
   d. Outputting the prediction to an electronic storage device.
   e. Optionally, using a visual indicator to alert the user (e.g., a pathologist, histology technician, etc.) to the presence of the biomarker.

Exemplary Embodiment: Continuous Score Prediction for Recurrence of Non-Invasive Breast Cancer Following diagnosis of non-invasive breast cancer, adjuvant treatment may be necessary after a patient has a lumpectomy or mastectomy. This treatment may include endocrine therapy or radiation treatment to reduce the risk recurrence, but these treatments have negative side effects. To determine the benefit a patient may have from these treatments, genomic assays have been developed.

A common form of non-invasive breast cancer is ductal carcinoma in situ (DCIS). Today, the primary genomic test for determining treatment options for DCIS is Oncotype DX DCIS, which is a 12-panel genomic test. This test produces a continuous score from 0 to 100 to determine the risk of breast cancer recurrence, with higher values indicating greater need for adjuvant treatment to prevent recurrence. Techniques presented herein may be used to predict this score by pairing WSI from patients that have DCIS with the continuous score produced by the genomic assay and then training the system to predict the score directly from WSI without the need for the genomic assay.

1. For training:
   a. Receive one or more digital WSI of a breast pathology specimen (e.g., histology, etc.) into a digital storage device (e.g., hard drive, network drive, cloud storage, RAM, etc.) and the continuous recurrence score. Optionally, patient information (e.g., age) may be received for each patient.
   b. Optionally, identify the salience of each region within the WSI, which may be the tumor and/or the stroma around the invasive tumor.
   c. Train a machine learning system to predict the continuous recurrence score from the (salient) image regions.
2. For use:
   a. Receive one or more digital images of a breast cancer pathology specimen (e.g., histology, etc.) into a digital storage device (e.g., hard drive, network drive, cloud storage, RAM, etc.). Optionally, patient information (e.g., age) may be received for each patient.
   b. Optionally, receive the location of salient region, which may be either automatically or manually specified by an expert.
   c. Apply the trained machine learning system to output a continuous prediction of cancer recurrence.
   d. Output the prediction to an electronic storage device.
   e. Optionally, use a visual indicator to alert the user (e.g., a pathologist, histology technician, etc.) to the predicted level of recurrence.
   f. Optionally, output recommended treatment for the patient.

Exemplary Embodiment: Continuous Score Prediction for Prostate Cancer Treatment Recommendation To diagnose prostate cancer, men receive a prostate biopsy and then the biopsy sample may be processed and then visually reviewed by a pathologist to determine the presence and severity of disease. However, prostate cancer treatments, e.g., removal of the prostate, hormone therapy, and/or radiation therapy, may have a negative impact on a man's quality of life, and some patients might not need aggressive treatment.

An alternative to only using pathologic assessment of prostate tissue samples may be to predict tumor aggressiveness using genomic assays. For example, the Oncotype DX Genomic Prostate Score may look at 17 genes to determine prostate cancer aggressiveness on a continuous score from 0 to 100. Patients with values closer to 0 may have active surveillance recommended whereas patients with higher scores should have immediate, aggressive treatment to reduce the risk of an adverse outcome (e.g., death or metastasis). Another test is the Prolaris assay, which combines genomic assessment with other measurements to determine a continuous score when a man can choose active surveillance for prostate cancer instead of aggressive treatment, where a higher score indicates the aggressiveness of the cancer. Techniques presented herein may be used to predict the prostate cancer aggressiveness scores by pairing WSI with the continuous score produced by any of these genomic assays and then training the system.

1. For training:
   a. Receive one or more digital images of a prostate pathology specimen into a digital storage device (e.g., hard drive, network drive, cloud storage, RAM, etc.) and the continuous aggressiveness score. Optionally, patient information (e.g., age) may be received for each patient.
   b. Optionally, identify the salience of each region within the WSI, e.g., the tumor and/or the stroma around the invasive tumor.
   c. Train a machine learning system to predict the continuous aggressiveness score from the (salient) image regions.
2. For use:
   a. Receive one or more digital images of a prostate cancer pathology specimen (e.g., histology, etc.) into a digital storage device (e.g., hard drive, network drive, cloud storage, RAM, etc.). Optionally, patient information (e.g., age) may be received for each patient.
   b. Optionally, receive the location of salient region, which may be either automatically or manually specified by an expert.
   c. Apply the trained machine learning system to output a continuous cancer aggressiveness score.
   d. Output the prediction to an electronic storage device.
   e. Optionally, use a visual indicator to alert the user (e.g., a pathologist, histology technician, etc.) to the predicted severity.
   f. Optionally, output recommended treatment for the patient.

Exemplary Embodiment: Predicting Continuous Scores for Likelihood of Malignancy from WSI Tumors are abnormal mass of cells, which may be benign or malignant. A benign tumor lacks the ability to metastasize or invade surrounding tissue, whereas a malignant tumor may do so. In some situations, pathological assessment does not suffice for determining if a tumor is malignant or benign. In this scenario, a continuous score may be used to better make the determination.

For example, the Myriad myPath Melanoma test measures 23 genes associated with cell differentiation, cell signaling, and immune response signaling to produce a continuous score on a scale of approximately −16 to 10, with scores greater than zero indicating the skin tumor may be likely to be malignant and that aggressive treatment may be needed whereas if the score is less than −2 it indicates the tumor may be likely benign. Techniques presented herein may be used to predict the myPath score by pairing WSI with the continuous score produced by the genomic assay and then training the system.

1. For training:
   a. Receive one or more digital images of a pathology specimen into a digital storage device (e.g., hard drive, network drive, cloud storage, RAM, etc.) and the continuous malignancy score. Optionally, patient information (e.g., age) may be received for each patient.
   b. Optionally, identify the salience of each region within the WSI.
   c. Train a machine learning system to predict the continuous malignancy score from the (salient) image regions.
2. For use:
   a. Receive one or more digital images of a pathology specimen (e.g., histology, etc.) into a digital storage device (e.g., hard drive, network drive, cloud storage, RAM, etc.). Optionally, patient information (e.g., age) may be received for each digital image.
   b. Optionally, receive the location of salient region, which may be either automatically or manually specified by an expert.
   c. Apply the trained machine learning system to output a continuous cancer malignancy score.
   d. Output the prediction to an electronic storage device.

e. Optionally, use a visual indicator to alert the user (e.g., a pathologist, histology technician, etc.) to the continuous malignancy score.

f. Optionally, output recommended treatment for the patient.

Exemplary Embodiment: Predicting Continuous Scores for Likelihood of Malignancy from Radiology Inputs While pathologic examination may be ideal, some tumors might not be easily accessible without causing harm to a patient and in other cases pathologists might not be available for review due to a lack of resources. In this scenario, it may be beneficial to predict malignancy as a continuous score from radiology data. This may be done by training a system to take as input radiology images (e.g., PET, CT, MRI, etc.) and output continuous malignancy scores which may be determined using outcome information.

1. For training:
   a. Receive one or more digital images of a radiology specimen into a digital storage device (e.g., hard drive, network drive, cloud storage, RAM, etc.) and the continuous malignancy score. Optionally, patient information (e.g., age) may be received for each patient.
   b. Optionally, identify the salience of each region within the radiologic scan.
   c. Train a machine learning system to predict the continuous malignancy score from the (salient) image regions.

2. For use:
   a. Receive one or more digital images of a radiology specimen into a digital storage device (e.g., hard drive, network drive, cloud storage, RAM, etc.). Optionally, patient information (e.g., age) may be received for each digital image.
   b. Optionally, receive the location of salient region, which may be either automatically or manually specified by an expert.
   c. Apply the trained machine learning system to output a continuous cancer malignancy score.
   d. Output the prediction to an electronic storage device.
   e. Optionally, use a visual indicator to alert the user (e.g., technician, clinician, etc.) to the continuous malignancy score.
   f. Optionally, output recommended treatment for the patient.

Exemplary Embodiment: Predicting Cancer Sub-Type from WSI as a Continuous Score

Determining the best course of treatment for a cancer may include determining its sub-type. For example, invasive breast cancer may be stratified into three sub-types luminal-type, HER2-type, and basal-type. Luminal-type typically indicates treatment via endocrine therapy, HER2-type indicates treatment via anti-HER2 based chemotherapy, and basal type (i.e., triple negative) breast cancer indicates that anti-HER2 chemotherapies and endocrine therapies would both be unhelpful.

However, cancers may often be characterized by type in a continuous manner. Rather than assuming a discrete category, the degree to which a cancer belongs to a specific type is fuzzy. Techniques presented herein may be used to sub-type cancers by producing multiple outputs that correspond to each type. For example, it may take as input a WSI for a patient and then be trained to predict the three continuous scores corresponding to luminal-type, HER2-type, and basal-type. The continuous values for each type may be determined using IHC, using genomic testing, using mass spectrometry, or some other method.

1. For training:
   a. Receive one or more digital images of a pathology specimen into a digital storage device (e.g., hard drive, network drive, cloud storage, RAM, etc.) and corresponding continuous scores for each type for the images. Optionally, patient information (e.g., age) may be received for each patient.
   b. Optionally, identify the salience of each region within the WSI.
   c. Train a machine learning system to predict multiple continuous scores for each type from the (salient) image regions.

2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the continuous scores corresponding to one or more known types for the cancer tissue.
   d. Output the prediction to an electronic storage device.
   e. Optionally, use a visual indicator to alert the user (e.g., a pathologist, histology technician, etc.) to the continuous subtype scores.
   f. Optionally, output recommended treatment for the patient.

Exemplary Embodiment: Predicting Homologous Recombination Deficiency (HRD) from WSI Homologous recombination genes regulate DNA repair pathways. Tumors that exhibit homologous recombination deficiency (HRD) have mutations associated with impaired DNA repair. Determining the continuous degree to which these HRD mutations are present may be used to guide treatment. For example, BRCA1 and BRCA2 mutations are two such HRD mutations. If HRD is sufficiently present, poly (ADP-ribose) polymerase (PARP) inhibitors may be used to treat a cancer, which keep cancer cells from repairing damaged DNA.

A continuous HRD score may be produced as a weighted or unweighted sum of gene mutations associated with impaired DNA repair. Techniques presented herein may be used to predict HRD directly from WSI of tumor pathology specimens by training it to take as input a WSI and output the HRD score determined via a genomic assay.

1. For training:
   a. Receive one or more digital images of a pathology specimen into a digital storage device (e.g., hard drive, network drive, cloud storage, RAM, etc.) and corresponding continuous HRD score for one or more images. Optionally, patient information (e.g., age) may be received for each patient.
   b. Optionally, identify the salience of each region within the WSI.
   c. Train a machine learning system to predict the continuous HRD score from the (salient) image regions.

2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the continuous HRD score.

d. Output the prediction to an electronic storage device.

e. Optionally, use a visual indicator to alert the user (e.g., a pathologist, histology technician, etc.) to the HRD score.

f. Optionally, output a breakdown of the specific genes that were mutated.

g. Optionally, output recommended treatment for the patient.

Exemplary Embodiment: Predicting Tumor Mutation Burden (TMB) from WSI

Tumor mutation burden (TMB) may be a continuous measurement of the mutations in a tumor and it may be a predictive biomarker that is associated with response to immune-oncology (IO) therapy. TMB may be determined using DNA sequencing of a tumor using whole exome sequencing, but this may be expensive and not always available. Techniques presented herein may be used to predict TMB directly from WSI of tumor pathology specimens by training it to take as input a WSI and output the TMB score determined via a genomic assay.

1. For training:
   a. Receive one or more digital images of a pathology specimen into a digital storage device (e.g., hard drive, network drive, cloud storage, RAM, etc.) and corresponding continuous TMB score for one or more of the images. Optionally, patient information (e.g., age) may be received for each patient.
   b. Optionally, identify the salience of each region within the WSI.
   c. Train a machine learning system to predict the continuous TMB score from the (salient) image regions.
2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the continuous TMB score.
   d. Output the prediction to an electronic storage device.
   e. Optionally, use a visual indicator to alert the user (e.g., a pathologist, histology technician, etc.) to the TMB score.
   f. Optionally, output recommended treatment for the patient.

Exemplary Embodiment: Predicting Mitotic and Cell Type Counts from WSI

Predicting the number of cells of a specific type may be useful as a biomarker and for histological grading. For example, in breast cancer a pathologist may be required to count mitoses within invasive breast cancer. Another example is tumor infiltrating lymphocytes (TILs), which are lymphocytic cells that have invaded tumor tissue and their presence may be associated with treatment outcome. There are a number of different kinds of TILs, including T cells, B cells, natural killer cells, macrophages, among others. Approaches for counting specific cell types within a tumor may require either manual visual inspection of pathology slides or use instance segmentation machine learning algorithms, which may require exhaustive pixel-wise annotation of a WSI. Techniques presented herein may be used to predict the counts of specific kinds of cells or mitoses directly from WSI without the need for exhaustive annotation of cell types or mitoses.

1. For training:
   a. Receive one or more digital images of a pathology specimen into a digital storage device (e.g., hard drive, network drive, cloud storage, RAM, etc.) and corresponding continuous counts for each cell type of interest.
   b. Optionally, identify the salience of each region within the WSI.
   c. Train a machine learning system to predict the cell counts of interest from the (salient) image regions. This may be done using regression (e.g., MSE, L2, Huber, etc.) or counting loss functions (e.g., Poisson loss).
2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the counts for each cell type of interest.
   d. Output the prediction to an electronic storage device.
   e. Optionally, use a visual indicator to alert the user (e.g., a pathologist, histology technician, etc.) to the counts of each cell type score.
   f. Optionally, provide a break-down of the percentage of one or more cell type found within a salient region and not within the salient region (e.g., within the tumor vs in the stroma).
   g. Optionally, output recommended treatment for the patient.

Exemplary Embodiment: Continuous and Ordinal HER2 Score Prediction

Tumors in a variety of different tissues may be driven by amplification or over-expression of the HER2 (ERBB2) oncogene, including breast, lung, and gastric cancer. The degree of amplification or over-expression may be used to determine which drugs are appropriate for treatment. For example, high levels of HER2 may indicate that a patient would benefit from treatment with the monoclonal antibody trastuzumab, a tumor that exhibits low-levels of HER2 over-expression or amplification may potentially be treated with fam-trastuzumab deruxtecan, and no HER2 over-expression or amplification indicates that alternative forms of treatment are warranted.

Techniques presented herein may be used to predict the level of HER2 over-expression on a continuous or ordinal scale directly from WSI of a patient's tumor. The level of expression may be determined using a variety of means which may be combined. These include multi-gene panels, mRNA expression, IHC, mass-spectrometry, etc. Subsequently, the expression level may either be treated as a continuous score or ordinal categories may be created, e.g., normal, low-levels of over-expression, and high-levels of over-expression.

1. For training:
   a. Receive one or more digital images of a cancer pathology specimen into a digital storage device (e.g., hard drive, network drive, cloud storage, RAM, etc.) and corresponding continuous or ordinal HER2 score for one or more WSI. These images may be of tissues stained with H&E, IHC, HES, etc.
   b. Optionally, identify the salience of each region within the WSI.
   c. Train a machine learning system to predict the continuous or ordinal HER2 score from the (salient) image regions.

2. For use:
   a. Receive one or more digital images of a cancer pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the HER2 expression score.
   d. Output the prediction to an electronic storage device.
   e. Optionally, use a visual indicator to alert the user (e.g., a pathologist, histology technician, etc.) to the HER2 expression score.
   f. Optionally, output recommended treatment for the patient.

Exemplary Embodiment: Prediction of Mass Spectrometry from WSI

Mass spectrometry may be used to measure the mass-to-charge ratio of one or molecules present in a biological specimen. This has been used in FFPE samples to measure proteins that are associated with biomarkers for drug targets. For example, HER2 protein levels may be measured using mass spectrometry, which may potentially be used to determine if an anti-HER2 chemotherapy would benefit a patient. Mass spectrometry produces the amount of an ion present, which may be measured on a continuous scale. Using mass spectrometry ground truth data, techniques presented herein may be used to predict the relative abundance of ions from WSI without the need to use a mass spectrometer.

1. For training:
   a. Receive one or more digital images of a breast cancer pathology specimen into a digital storage device (e.g., hard drive, network drive, cloud storage, RAM, etc.) and corresponding mass spectrometry score(s) for each WSI. These images may be of tissues stained with H&E, IHC, HES, etc.
   b. Optionally, identify the salience of each region within the WSI.
   c. Train a machine learning system to predict the continuous mass spectrometry values of interest.
2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the mass spectrometry values.
   d. Output the prediction to an electronic storage device.
   e. Optionally, use a visual indicator to alert the user (e.g., a pathologist, histology technician, etc.) to the values.

Exemplary Embodiment: Prediction of mRNA Levels from WSI

Messenger RNA (mRNA) levels are continuous values that quantify the level at which a particular gene is expressed. For oncology applications, quantifying the mRNA levels of oncogenes may be used to guide treatment. Levels of mRNA expression may be quantitatively measured using a variety of techniques, including northern blotting, RT-qPCR, serial analysis of gene expression (SAGE), and RNA-Seq. All of these tests have differing advantages and disadvantages, but they all may require considerable additional processing of the tissue. Techniques presented herein may be used to avoid this additional processing by directly predicting mRNA levels of tumors and other tissues directly from WSI 1. For training:
   a. Receive one or more digital images of a breast cancer pathology specimen (e.g., histology, etc.) into a digital storage device (e.g., hard drive, network drive, cloud storage, RAM, etc.) and corresponding mRNA levels for the genes of interest for each WSI. These images may be of tissues stained with H&E, IHC, HES, etc.
   b. Optionally, identify the salience of each region within the WSI.
   c. Train a machine learning system to predict the continuous mRNA levels.
2. For use:
   a. Receive one or more digital images of a pathology specimen into a digital storage device (e.g., hard drive, network drive, cloud storage, RAM, etc.)
   b. Optionally, receive the location of salient region, which may be either automatically or manually specified by an expert.
   c. Apply the trained machine learning system to output the mRNA levels.
   d. Output the prediction to an electronic storage device.
   e. Optionally, use a visual indicator to alert the user (e.g., a pathologist, technician, etc.) to the values.

Exemplary Embodiment: Gene Expression Value Prediction from WSI

Genomic test results may be helpful guides for treatment selection. One such result, gene expression value, may be obtained through microarray analysis followed by numerical processing. Microarray analysis of solid tumors is challenging, as preparation of the FPPE tissue sample may result in fragmentation of the genomic DNA extracted from the sample, which may introduce noise into the process. To handle this problem, the have been numerous normalization methods proposed in the literature. Techniques presented herein may be used to bypass the microarray analysis and predict gene expression value directly from WSI.

1. For training:
   a. Receive one or more digital images of a breast cancer pathology specimen (e.g., histology, etc.) into a digital storage device (e.g., hard drive, network drive, cloud storage, RAM, etc.) and corresponding gene expression values for the genes of interest for each WSI. These images may be of tissues stained with H&E, IHC, HES, etc.
   b. Optionally, identify the salience of each region within the WSI.
   c. Train a machine learning system to predict the continuous gene expression values.
2. For use:
   a. Receive one or more digital images of a pathology specimen into a digital storage device (e.g., hard drive, network drive, cloud storage, RAM, etc.)
   b. Optionally, receive the location of salient region, which may be either automatically or manually specified by an expert.
   c. Apply the trained machine learning system to output the gene expression values.
   d. Output the prediction to an electronic storage device.
   e. Optionally, use a visual indicator to alert the user (e.g., a pathologist, technician, etc.) to the values.

Exemplary Embodiment: NTRK Gene Fusion Prediction from WSI

Neurotrophic Receptor Tyrosine Kinase (NTRK) is a family of 3 genes encoding tropomyosin receptor kinases.

Rearrangements involving these genes, called NTRK gene fusions, lead to abnormal proteins called TRK fusion proteins which, in turn, may lead to the formation and growth of cancer. Detection of these gene fusions may be valuable, since patients with NTRK gene fusions have been shown to respond very positively to TRK inhibitor therapy. Detection of these gene fusions from FFPE tissue may be achieved by a variety of methods, such as Pan-TRK IHC, FISH, RT-PCR, DNA and/or RNA-based NGS, each with advantages and disadvantages. Given a continuous score for NTRK gene fusion calculated by any method, techniques presented herein may be used to calculate that score from WSI.

1. For training:
   a. Receive one or more digital images of a breast cancer pathology specimen (e.g., histology, etc.) into a digital storage device (e.g., hard drive, network drive, cloud storage, RAM, etc.) and corresponding NTRK gene fusion scores for each WSI. These images may be of tissues stained with H&E, IHC, HES, etc.
   b. Optionally, identify the salience of each region within the WSI.
   c. Train a machine learning system to predict the continuous NTRK gene fusion scores.
2. For use:
   a. Receive one or more digital images of a pathology specimen into a digital storage device (e.g., hard drive, network drive, cloud storage, RAM, etc.)
   b. Optionally, receive the location of salient region, which may be either automatically or manually specified by an expert.
   c. Apply the trained machine learning system to output the NTRK gene fusion scores.
   d. Output the prediction to an electronic storage device.
   e. Optionally, use a visual indicator to alert the user (e.g., a pathologist, technician, etc.) to the values.

Exemplary Embodiment: Predicting Microsatellite Instability (MSI) from WSI

Microsatellite instability (MSI) is a continuous value that indicates the level of impaired DNA mismatch repair (MMR) present in a tissue. MMR fixes errors during DNA replication, and the degree of MSI present may be associated with cancer treatment outcome. For example, colon cancers with high levels of MSI have a better prognosis than those with low levels. Traditionally, determining the level of MSI may have required DNA sequencing. However, using techniques presented herein, the MSI level may be predicted from images of pathology specimens without the time and expense required for DNA sequencing.

1. For training:
   a. Receive one or more digital images of a pathology specimen into a digital storage device (e.g., hard drive, network drive, cloud storage, RAM, etc.) and corresponding continuous MSI score for one or more of the images. MSI scores may be derived via DNA sequencing. Optionally, patient information (e.g., age) may be received for each patient.
   b. Optionally, identify the salience of each region within the WSI for where the MSI determination should be made.
   c. Train a machine learning system to predict the continuous MSI score from the (salient) image regions.
2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the continuous MSI score.
   d. Output the prediction to an electronic storage device.
   e. Optionally, use a visual indicator to alert the user (e.g., a pathologist, histology technician, etc.) to the MSI score.
   f. Optionally, output recommended treatment for the patient.

Exemplary Embodiment: Predicting Continuous PDL1 Expression Levels from WSI

PDL1 is a biomarker being used to assess whether a patient will likely to respond to immunotherapies. It is being tested through an IHC test and the presence of PDL1 in the tumor and/or in immune cells are being used to determine patient's likelihood of response to these therapies. Techniques presented herein may be used to assess patient's PDL1 expression levels in a more reliable fashion from WSI's.

1. For training:
   d. Receive one or more digital images of a pathology specimen into a digital storage device (e.g., hard drive, network drive, cloud storage, RAM, etc.) and corresponding PDL1 expression for one or more of the images. PDL1 expression levels may be assessed through PDL1 IHC images by either manually by pathologists or by assessing PDL1 expression levels through image analysis solutions.
   e. Optionally, identify the salience of each region within the WSI for where PDL1 determination should be made.
   f. Train a machine learning system to predict the continuous PDL1 expression level from the (salient) image regions.
2. For use:
   a. Receive one or more digital images of a pathology specimen (e.g., histology, etc.) into a digital storage device (e.g., hard drive, network drive, cloud storage, RAM, etc.)
   b. Optionally, receive the location of salient region, which may be either automatically or manually specified by an expert.
   c. Apply the trained machine learning system to output the continuous PDL1 expression level.
   d. Output the prediction to an electronic storage device.
   e. Optionally, use a visual indicator to alert the user (e.g., a pathologist, histology technician, etc.) to the PDL1 expression level.
   f. Optionally, output recommended treatment for the patient.

Exemplary Embodiment: Predicting Tumor Inflammation Signature (TIS) from WSI

Tumor inflammation signature (TIS) is an 18 gene signature measuring the pathways associated with a suppressed adaptive immune response and has been shown to enrich for response to immune checkpoint inhibitors (ICI)'s. Techniques presented herein may be used to measure TIS score which will help evaluate patient's likelihood of response to ICI's from WSI's.

1. For training:
   a. Receive one or more digital images of a pathology specimen into a digital storage device (e.g., hard drive, network drive, cloud storage, RAM, etc.) and corresponding TIS for one or more of the images. TIS may be assessed through mRNA expression levels of the tumor.
b. Optionally, identify the salience of each region within the WSI for where TIS determination should be made.
c. Train a machine learning system to predict TIS score from the (salient) image regions.
2. For use:
a. Receive one or more digital images of a pathology specimen (e.g., histology, etc.) into a digital storage device (e.g., hard drive, network drive, cloud storage, RAM, etc.)
b. Optionally, receive the location of salient region, which may be either automatically or manually specified by an expert.
c. Apply the trained machine learning system to output TIS score.
d. Output the prediction to an electronic storage device.
e. Optionally, use a visual indicator to alert the user (e.g., a pathologist, histology technician, etc.) to TIS score.
f. Optionally, output recommended treatment for the patient.

Figure 9:
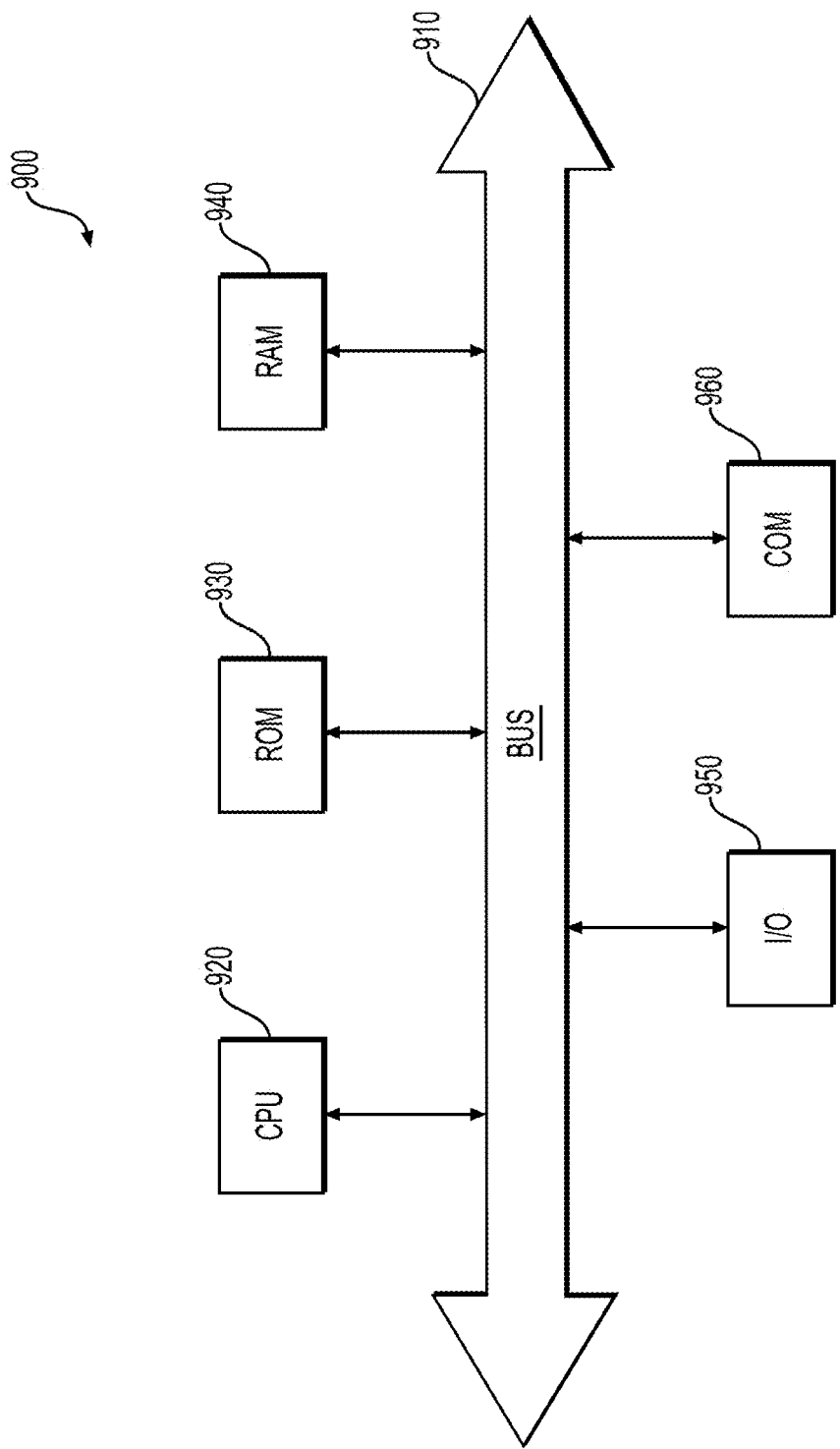
FIG. 9 illustrates an example system that may execute techniques presented herein.

As shown in FIG. 9, device 900 may include a central processing unit (CPU) 920. CPU 920 may be any type of processor device including, for example, any type of special purpose or a general-purpose microprocessor device. As will be appreciated by persons skilled in the relevant art, CPU 920 also may be a single processor in a multi-core/multi-processor system, such system operating alone, or in a cluster of computing devices operating in a cluster or server farm. CPU 920 may be connected to a data communication infrastructure 910, for example a bus, message queue, network, or multi-core message-passing scheme.

Device 600 may also include a main memory 940, for example, random access memory (RAM), and also may include a secondary memory 930. Secondary memory 930, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include similar means for allowing computer programs or other instructions to be loaded into device 900. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 900.

Device 900 also may include a communications interface ("COM") 960. Communications interface 960 allows software and data to be transferred between device 600 and external devices. Communications interface 960 may include a modem, a network interface (such as an Ethernet card), a communications port, a PCMCIA slot and card, or the like. Software and data transferred via communications interface 960 may be in the form of signals, which may be electronic, electromagnetic, optical or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 900 may also include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

What is claimed is:
1. A computer-implemented method for using processed images to train a machine learning system to process medical images, the method comprising:
receiving one or more digital medical images;
identifying at least one salient region corresponding to the one or more digital medical images; and
upon identifying the at least one salient region, training the machine learning system to predict at least one continuous value from the at least one salient region, the training further comprising:
extracting at least one diagnostic feature vector/tensor from the at least one salient region, wherein the at least one diagnostic feature vector/tensor is collected at multiple resolutions to create pyramids of feature vectors and provide hierarchical spatial information;
appending a spatial coordinate of each pixel and/or voxel of the at least one salient region to a corresponding at least one diagnostic feature vector/tensor; and based on the at least one diagnostic feature vector/tensor, outputting and/or storing the at least one continuous value.

2. The computer-implemented method of claim 1, the identifying the at least one salient region further comprising:
receiving salient training data, the salient training data including an indication of a presence or an absence of a salient region within the one or more digital medical images;
breaking each of the one or more digital medical images into at least one region; and
predicting that the at least one region is the at least one salient region.

3. The computer-implemented method of claim 2, wherein the salient training data further includes a location of the salient region.

4. The computer-implemented method of claim 3, wherein the location of the salient region is specified with at least one of: a pixel-level label, a bounding box-based label, a polygon-based label, a corresponding image where saliency has been identified, a voxel-level label, a subvoxel-level label, and/or a deformed template.

5. The computer-implemented method of claim 2, wherein the breaking is done by at least one of: creating at least one tile of the one or more digital medical images, a segmentation based on an edge and/or contrast, a color segmentation based on at least one color difference, an energy segmentation based on an energy minimization, a supervised determining by the machine learning system, and/or an EdgeBox.

6. The computer-implemented method of claim 1, wherein the machine learning system is at least one of: a Convolutional Neural Network, a CoordConv algorithm, a Capsule Neural Network, a Random Forest Algorithm, a Support Vector Machine, and/or a multi-layer perceptron.

7. The computer-implemented method of claim 1, wherein receiving the one or more digital medical images further comprises:
receiving patient information, wherein the patient information comprises at least one of: an age, an ethnicity, and/or an ancillary test result.

8. The computer-implemented method of claim 1, wherein the one or more digital medical images comprise at least one of: a whole slide image (WSI), a magnetic resonance imaging (MRI) scan, a computed tomography (CT) scan, a positron emission topography (PET) scan, and/or a mammogram.

9. The computer-implemented method of claim 1, wherein the at least one continuous value corresponds to a continuous biomarker value.

10. The computer-implemented method of claim 1, wherein the at least one salient region comprises a tissue or blood region associated with a pathological condition, a cancerous region, one or more biomarkers, specific cell types, particular protein presence, and/or at least one drug response indicator.

11. A computer system for using processed images to train a machine learning system to process medical images, the computer system comprising:
at least one memory storing instructions; and
at least one processor configured to execute the instructions to perform operations comprising:
access the at least one memory and execute processor-readable instructions, which when executed by the at least one processor configures the at least one processor to perform a plurality of functions, including functions for:
receiving one or more digital medical images;
identifying at least one salient region corresponding to the one or more digital medical images; and
upon identifying the at least one salient region, training the machine learning system to predict at least one continuous value from the at least one salient region, the training further comprising:
extracting at least one diagnostic feature vector/tensor from the at least one salient region, wherein the at least one diagnostic feature vector/tensor is collected at multiple resolutions to create pyramids of feature vectors and provide hierarchical spatial information;
appending a spatial coordinate of each pixel and/or voxel of the at least one salient region to a corresponding at least one diagnostic feature vector/tensor; and
based on the at least one diagnostic feature vector/tensor, outputting and/or storing the at least one continuous value.

12. The computer system of claim 11, the identifying the at least one salient region further comprising:
receiving salient training data, the salient training data including an indication of a presence or an absence of a salient region within the one or more digital medical images;
breaking each of the one or more digital medical images into at least one region; and
predicting that the at least one region is the at least one salient region.

13. The computer system of claim 12, wherein the salient training data further includes a location of the salient region.

14. The computer system of claim 13, wherein the location of the salient region is specified with at least one of: a pixel-level label, a bounding box-based label, a polygon-based label, a corresponding image where saliency has been identified, a voxel-level label, a subvoxel-level label, and/or a deformed template.

15. The computer system of claim 12, wherein the breaking is done by at least one of: creating at least one tile of the one or more digital medical images, a segmentation based on an edge and/or contrast, a color segmentation based on at least one color difference, an energy segmentation based on an energy minimization, a supervised determining by the machine learning system, and/or an EdgeBox.

16. A non-transitory computer-readable medium containing instructions that, when executed by a processor, cause the processor to perform operations for using processed images to train a machine learning system to process medical images, the operations comprising:
receiving one or more digital medical images;
identifying at least one salient region corresponding to the one or more digital medical images; and
upon identifying the at least one salient region, training the machine learning system to predict at least one continuous value from the at least one salient region, the training further comprising:
extracting at least one diagnostic feature vector/tensor from the at least one salient region, wherein the at least one diagnostic feature vector/tensor is collected at multiple resolutions to create pyramids of feature vectors and provide hierarchical spatial information;
appending a spatial coordinate of each pixel and/or voxel of the at least one salient region to a corresponding at least one diagnostic feature vector/tensor; and based on the at least one diagnostic feature vector/tensor, outputting and/or storing the at least one continuous value.

17. The non-transitory computer-readable medium of claim 16, the identifying the at least one salient region further comprising:
    receiving salient training data, the salient training data including an indication of a presence or an absence of a salient region within the one or more digital medical images;
    breaking each of the one or more digital medical images into at least one region; and
    predicting that the at least one region is the at least one salient region.

18. The non-transitory computer-readable medium of claim 16, wherein receiving the one or more digital medical images further comprises:
    receiving patient information, wherein the patient information comprises at least one of: an age, an ethnicity, and/or an ancillary test result.

19. The non-transitory computer-readable medium of claim 16, wherein the one or more digital medical images comprise at least one of: a whole slide image (WSI), a magnetic resonance imaging (MRI) scan, a computed tomography (CT) scan, a positron emission topography (PET) scan, and/or a mammogram.

* * * * *